United States Patent [19]
Delcuve

[11] Patent Number: 5,888,774
[45] Date of Patent: Mar. 30, 1999

[54] RECOMBINANT DNA MOLECULES AND EXPRESSION VECTORS FOR ERYTHROPOIETIN

[75] Inventor: Geneviève Delcuve, Manitoba, Canada

[73] Assignee: Cangene Corporation, Winnipeg, Canada

[21] Appl. No.: 358,918

[22] Filed: Dec. 19, 1994

[51] Int. Cl.$^6$ ............... C12P 21/00; C12N 5/00; C12N 15/00

[52] U.S. Cl. ............ 435/69.6; 435/172.3; 435/320.1; 435/240.2; 935/11; 935/34

[58] Field of Search ............ 536/23.1, 24.1; 435/172.3, 240.2, 320.1, 69.6; 935/11, 24, 34, 70, 71

[56] References Cited

U.S. PATENT DOCUMENTS

| | | |
|---|---|---|
| 4,677,195 | 6/1987 | Hewick et al. . |
| 4,703,008 | 10/1987 | Lin . |
| 5,304,489 | 4/1994 | Rosen . |
| 5,322,837 | 6/1994 | Hewick et al. . |

FOREIGN PATENT DOCUMENTS

| | | |
|---|---|---|
| 1309043 | 10/1992 | Canada . |
| 0 232 034 | 8/1987 | European Pat. Off. . |
| 0 236 059 | 9/1987 | European Pat. Off. . |
| 0 267 678 | 5/1988 | European Pat. Off. . |
| WO 85/02610 | 6/1985 | WIPO . |
| WO 86/03520 | 6/1986 | WIPO . |
| WO 88/00241 | 1/1988 | WIPO . |

OTHER PUBLICATIONS

Tsao et al., Ann. N.Y. Acad. Sci., 665:127–136, 1992.
Semenza et al., Mol. Cell. Biol., 10:930–938, 1990.
Jacobs, et al., 1985, Nature (Lond.) 313:806.
Lin, 1985, Proc. Natl. Acad. Sci. 82:7580.
Lee–Huang, 1984, Proc. Natl. Acad. Sci. 81:2708.
Goto et al., 1988, Biotechnology 6:67.
McDonald, 1990, Crit. Rev. Biotech. 10:155.
Powell, et al., 1986, Proc. Natl. Acad. Sci. 83:6465.
Yanagi, et al., 1989, DNA 8: 419.
Phi–Van and Strätling, Prog. Mol. Subcell. Biol. 11:1–11, 1990.
Stief, et al., Nature 341:343–345, 1989.
Phi–Van, et al., Mol. Cell. Biol., 10:2302–2307, 1990.
Klehr, et al., Biochemistry, 30:1264–1270, 1991.
Levy–Wilson and Fortier, 1989, J. Biol. Chem. 264:21196.
Cockerill and Garrard, 1986, Cell 44, 273–282.
McKnight et al., Proc. Natl. Acad. Sci. U.S.A. 89:6943, 1992.
Brooks, et al., Mol. Cell. Biol. 14:2243, 1994.
Gasser et al., International Review of Cytology, 119:57, 1989.
Keay et al., Appl. Microbiol. Biotechnol., 34:198, 1990.
Allen et al., The Plant Cell, 5:603, 1993.
Bode and Maass, Biochemistry, 27:4706, 1988.
Phi–Van and Strätling, EMBO Journal, 7:655, 1988.
Bode et al., Science, 255:195, 1992.
Mislke et al., Biochemistry, 29:7475, 1990.
Kelhr et al., Biochemistry, 31:3223, 1992.
Driel et al., J. of Cell. BioChem., 47:311, 1991.
Laemmli et al., Genetics and Development, 2:275, 1992.
Zlatanova and Holde, Eukaryotic Gene Expression, 2:211, 1992.
Boulikas, Teni, J. of Cell. Biochem. 52:14, 1993.
Yanagi et al., Gene, 76:19, 1989.

*Primary Examiner*—Jasemine C. Chambers
*Attorney, Agent, or Firm*—Bereskin & Parr

[57] ABSTRACT

A recombinant DNA molecule adapted for transfection of a host cell comprising a nucleic acid molecule encoding mammalian erythropoietin, an expression control sequence operatively linked thereto and at least one SAR element. The invention also relates to expression vectors having the recombinant DNA molecule and to mammalian cells transformed with the expression vector. The mammalian cells lack multiple copies of an amplified amplification gene and are capable of expressing recombinant EPO in vitro at levels of at least 1,500 u/$10^6$ cells in 24 hours. The invention further relates to a method of expressing recombinant mammalian erythropoietin using the expression vectors and to a transgenic non-human animal or embryo whose germ cells and somatic cells contain a DNA construct having the recombinant DNA molecule of the invention.

17 Claims, 14 Drawing Sheets

FIGURE 1B

| OLIGONUCLEOTIDE | SEQUENCE | SEQUENCE POSITION (as per AMGEN patent cDNA) |
|---|---|---|
| EPO1 | 5'- AGC TTG CCC GGG ATG AGG GCC ACC GGT GTG GTC ACC CGG CGC GCC CCA GGT | 111 - 153 |
| EPO2 | 5'- CGC TGA GGG ACC CCG GCC AGG CGC GGA GAT GGG GGT GCA CGA AT | 154 - 197 |
| EPO3 | 5'- GTC CTG CCT GGC TGT GGC TTC TCC TGT CCC TGC TGT CGC TCC CTC TGG GCC | 198 - 248 |
| EPO4 | 5'- TCC CAG TCC TGG GCG CCC CAC CAC GCC TCA TCT GTG ACA GCC GAG TCC TGG AGA GGT AC | 249 - 307 |
| EPO5 | 5'- CTC TTG GAG GCC AAG GAG GCC GAG AAT ATC ACG ACG GGC TGT GCT GAA CAT TGC AG | 308 - 363 |
| EPO6 | 5'- CTT GAA TGA GAA TAT CAC TGT CCC AGA CAC CAA AGT TAA TTT CTA TGC CTG GAA GAG G | 364 - 421 |
| EPO7 | 5'- ATG GAG GTC GGG CAG CAG GCC GTA GAA GTC TGG CAG GGC CTG GCC CTG CTG TCG G | 422 - 476 |
| EPO8 | 5'- AAG CTG TCC TGC GGG GCC AGG CCC TGT TGG TCA ACT CTT CCC AGC CGT GGG AGC CCC TGC A | 477 - 537 |
| EPO9 | 5'- GCT GCA TGT GGA TAA AGC CGT CAG TGG CCT TCG CAG CCT CAC CAC TCT GCT TCG | 538 - 591 |
| EPO10 | 5'- GGC TCT GGG AGC CCA GAA GGA AGC CAT CTC CCC TCC AGA TGC GGC CTC AGC | 592 - 642 |
| EPO11 | 5'- TGC TCC ACT CCG AAC AAT CAC TGC TGA CAC TTT CCG CAA ACT CTT CCG AGT | 643 - 693 |
| EPO12 | 5'- CTA CTC CAA TTT CCT CCG GGG AAA GCT GAA GCT GTA CAC AGG GGA GG | 694 - 740 |
| EPO13 | 5'- CCT GCA GGA CAG GGG ACA GAT GAC CAG GTG TGT CGA CCT GGG CAT ATC | 741 - 788 |
| EPO13b | 5'- CCT GCA GGA CAG GGG ACA GAT GAC CAG GTG TGT CCA CCT GGG CAT ATC | 741 - 788 |
| EPO14 | 5'- CAC CAC CTC CCT CAC CAA TAT TGC TTG TGC CAC ACC CTC CCC CGC CAC TC | 789 - 838 |

FIGURE 1C

| OLIGONUCLEOTIDE | SEQUENCE | SEQUENCE POSITION (as per AMGEN patent cDNA) |
|---|---|---|
| EPO15 | 5'- CTG AAC CCC GTC GAG GGG CTC TCA GCT CAG CGC CAG CCT GTC CCA TGG ACC A | 839-888 |
| EPO1α | 5'- CCT CAG CGA CCT GGG GCG CGC CGG GTG ACC ACA CCG GTG GCC CTC ATC CCG GGC A | 111-161 |
| EPO2α | 5'- GGC AGG ACA TTC GTG CAC CCC CAT CTC CGC GCC TGG CCG GGG TC | 162-205 |
| EPO3α | 5'- GGA CTG GGA GGC CCA GAG GGA GCG ACA GCA GGG ACA GGA GAA GCC ACA GCC A | 206-257 |
| EPO4α | 5'- CTC TCC AGG ACT CGG CTG TCA CAG ATG AGG CGT GGT GGG GCG CCC A | 258-303 |
| EPO5α | 5'- TTC AGC ACA GCC CGT CGT GAT ATT CTC GGC CTC CTT GGC CTC CAA GAG GTA C | 304-355 |
| EPO6α | 5'- AGG CAT AGA AAT TAA CTT TGG TGT CTG GGA CAG TGA TAT TCT CAT TCA AGC TGC AAT G | 356-413 |
| EPO7α | 5'- AGG GCC AGG CCC TGC CAG ACT TCT ACG GCC TGC TGC CCG ACC TCC ATC CTC TTC C | 414-468 |
| EPO8α | 5'- GGG GCT CCC ACG GCT GGG AAG AGT TGA CCA ACA GGG CCT GGC CCC GCA GGA CAG CTT CCG ACA GC | 469-533 |

FIGURE 1D

| OLIGONUCLEOTIDE | SEQUENCE | SEQUENCE POSITION (as per AMGEN patent cDNA) |
|---|---|---|
| EPO9α | 5'- AGT GGT GAG GCT GCG AAG GCC ACT GAC GGC TTT ATC CAC ATG CAG CTG CA | 534-583 |
| EPO10α | 5'- CGC ATC TGG AGG GGA GAT GGC TTC CTT CTG GGC TCC CAG AGC CCG AAG CAG | 584-634 |
| EPO11α | 5'- AGA CTC GGA AGA GTT TGC GGA AAG TGT CAG CAG TGA TTG TTC GGA GTG GAG CAG CTG AGG C | 635-695 |
| EPO12α | 5'- CCT GCA GGC CTC CCC TGT GTA CAG CTT CAG CTT TCC CCG AGG GAA ATT GGA GT | 696-748 |
| EPO13α | 5'- GGT GGT GGA TAT GCC CAG GTC GAC ACA CCT GGT CAT CTG TCC CCT GT | 749-795 |
| EPO13bα | 5'- GGT GGT GGA TAT GCC CAG GTG GAC ACA CCT GGT CAT CTG TCC CCT GT | 749-795 |
| EPO14α | 5'- GGG TTC AGG AGT GGC GGG GGA GGG TGT GGC ACA AGC AAT ATT GGT GAG GGA | 796-846 |
| EPO15α | 5'- AGC TTG GTC CAT GGG ACA GGC TGG CGC TGA GCT GAG AGC CCC TCG ACG | 847-888 |

FIGURE 3A

```
   1 aagcttctgg gcttccagac ccagctactt tgcggaactc agcaacccag gcatctctga
  61 gtctccgccc aagaccggga tgcccccag  gggaggtgtc cgggagccca gcctttccca
 121 gatagcacgc tccgccagtc ccaaggtgc  gcaaccggct gcactcccct cccgcgaccc
 181 agggcccggg agcagcccc  atgacccaca cgcacgtctg cagcagcccc gctcacgccc
 241 cggcgagcct caacccaggc gtcctgcccc tgctctgacc ccggtgcc   cctaccctg
 301 gcgaccctc  acgcacacag cctctccccc accccacc   gcgcacgcac acatgcagat
 361 aacagccccg accccccggc agagccgcag agtccctggg ccaccccgc  cgctcgctgc
 421 gctgcgcgc  accgcgctgt cctcccgag  ccggaccggg gccaccgcgc ccgctctgct
 481 ccgacaccgc gccccctga  cagccgcct  ctcctctagg ccgtgggc   tggccctgca
 541 ccgccgagct tcccggatg  agggcccccg gtgtggtcac ccggcgcgcc ccaggtcgct
 601 gagggacccc ggccaggcgc ggagatgggg gtgcacggtg agtactcgcg ggcttgggcgc
 661 tcccgcgcc  cggtccctg  tttgagcggg gatttagcgc cccggctatt ggccaggagg
 721 tggctgggtt caaggaccgg cgacttgtca aggaccccgg aagggggagg gggtggggc
 781 agcctccacg tgccagcggg gacttggggg agtccttggg gatggcaaaa acctgacctg
 841 tgaaggggac acagtttggg ggttgaggtt gggggttctg ctgtgccagt
 901 ggagaggaag ctgataagct gataaacctg gcgctggagc caccacttat ctgccagagg
 961 ggaagcctct gtcacacacg gattgaagtt tggccggaga agt.ggatgct ggtagctggg
1021 ggtggggtgt gcacacggca gcaggattga atgaaggcca gggaggcagc acctgagtgc
1081 ttgcatggtt gggacagga  aggacgagct gggcagaga  cgtgggatg  aaggaagctg
1141 tccttccaca gccaccttc  tcccctcccg cctgactctc agcctggcta tctgttctag
1201 aatgtcctgc ctggctgtgg cttctccctgt ccctgctgtc gctccctctg ggcctcccag
1261 tcctgggcgc cccaccacg  ctcatctgtg acagccgagt cctggagagg tacctcttgg
1321 aggccaagga ggccgagaat atcacggtga gacccctcc  ccagcacatt ccacagaact
1381 cacgctcagg gcttcaggga actcctccca gatccaggaa cctggcactt ggtttggggt
1441 ggagttggga agctagacac tgccccccta cataagaata agtctgttgg ccccaaacca
1501 tacctggaaa ctaggcaagg agcaaagcca gcagatccta cggcctgtgg cggcaggcca
1561 gagccttcag ggaccccttga ctcccccggg tgtgtgcatt tcagacgggc tgtgctgaac
1621 actgcagctt gaatgagaat atcactgtcc cagcaccaa  agttaatttc tatgcctgga
1681 agaggatgga ggtgagttcc ttttttttt  tttttccttt ctttggaga  atctcatttg
1741 cgagcctgat tttggatgaa agggagaatg atcgggggaa aggtaaaatg gagcagcaga
1801 gatgaggctg cctgggcgca gaggctcacg tctataatcc caggctgaga tggccgagat
```

FIGURE 3B

```
1861 gggagaattg cttgagccct ggagtttcag accaacctag gcagcatagt gagatccccc
1921 atctctacaa acatttaaaa aaattagtca gtgaagtgg tgcatggtgg tagtcccaga
1981 tatttggaag gctgaggcgg gaggatcgct tgagcccagg aatttgaggc tgcagtgagc
2041 tgtgatcaca ccactgcact ccagcctcag tgacagagtg agccctgtc tcaaaaaaga
2101 aaagaaaaaa gaaaaataat gaggctgta tggaatacat tcattattca ttcactcact
2161 cactcactca ttcattcatt cattcattca acaagtctta ttgcatacct tctgtttgct
2221 cagcttgtg cttggggctg ctgagggca gaggggagag ggtgacatgg gtcagctgac
2281 tcccagagtc cactccctgt aggtcgggca gcaggccgta gaagtctggc agggcctggc
2341 cctgctgtcg gaagctgtcc tgcggggcca ggccctgttg gtcaactctt cccagccgtg
2401 ggagccctg cagctgcatg tggataaagc cgtcagtgc cttcgcagcc tcaccactct
2461 gcttcgggct ctgggagccc agtgagtag gagcggacac ttctgcttgc cctttctgta
2521 agaaggggag aagggtcttg ctaaggagta caggaactgt ccgtattcct tccctttctg
2581 tggcactgca gcgacctcct gttttctcct tggcagaagg aagccatctc ccctccagat
2641 gcggcctcag ctgctccact ccgaacaatc actgctgaca ctttccgcaa actcttccga
2701 gtctactcca atttcctccg gggaaagctg aagctgtaca caggggaggc ctgcaggaca
2761 ggggacagat gaccaggtgt gtccacctgg gcatatccac cacctccctc accaacattg
2821 cttgtgccac acctcccccc gccactcctg aaccccgtcg agggctctc agctcagcgc
2881 cagcctgtcc catggacact ccagtgccag caatgacatc tcagggcca gaggaactgt
2941 ccagagagca actctgagat ctaaggatt cacaggcca acttgagggc ccagagcagg
3001 aagcattcag agagcagctt taaactcagg gacagagcca tgctgggaag acgcctgagc
3061 tcactcggca cctgcaaaa tttgatgcca ggacacgctt tggaggcgat ttacctgttt
3121 tcgcacctac catcaggac aggatgacct ggagaactta ggtggcaagc tgtgacttct
3181 ccaggtctca cgggcatggg cactccctg gtggcaagag cccccttgac accggggtgg
3241 tgggaaccat gaagacagga tggggctgg cctctggctc tcatggggtc caagttttgt
3301 gtattcttca acctcattga caagaactga aaccaccaat atgactcttg gctttctgt
3361 tttctgggaa cctccaaatc ccctgctct gtcccactcc tggcagcagt gcagcaggtc
3421 caggtccggg aaatgagggg tggaggggc tgggcctac tggcctgtctc acacagcctg
3481 tctgacctct cgacctaccg gcctaggcca caagctctgc ctacgctggt caataaggtg
3541 tctccattca aggcctcacc gcagtaaggc agctgccaac agctgccagg gcaaggctgc
3601 ag
```

FIGURE 3C

MGVHECPAWLWLLLSLLSLPLGLPVLGAPPRLICDSRVLERYLLEAKEAENITTGCAEHC

SLNENITVPDTKVNFYAWKRMEVGQQAVEVWQGLALLSEAVLRGQALLVNSSQPWEPLQL

HVDKAVSGLRSLTTLLRALGAQKEAISPPDAASAAPLRTITADTFRKLFRVYSNFLRGKL

KLYTGEACRTGDR

FIGURE 4

```
AGCTTGCCCG GGATGAGGGC CACCGGTGTG GTCACCCGGC GCGCCCCAGG TCGCTGAGGG    60
ACCCCGGCCA GGCGCGGAGA TGGGGGTGCA CGAATGTCCT GCCTGGCTGT GGCTTCTCCT   120
GTCCCTGCTG TCGCTCCCTC TGGGCCTCCC AGTCCTGGGC GCCCCACCAC GCCTCATCTG   180
TGACAGCCGA GTCCTGGAGA GGTACCTCTT GGAGGCCAAG GAGGCCGAGA ATATCACGAC   240
GGGCTGTGCT GAACATTGCA GCTTGAATGA GAATATCACT GTCCCAGACA CCAAAGTTAA   300
TTTCTATGCC TGGAAGAGGA TGGAGGTCGG GCAGCAGGCC GTAGAAGTCT GGCAGGGCCT   360
GGCCCTGCTG TCGGAAGCTG TCCTGCGGGG CCAGGCCCTG TTGGTCAACT CTTCCCAGCC   420
GTGGGAGCCC CTGCAGCTGC ATGTGGATAA AGCCGTCAGT GGCCTTCGCA GCCTCACCAC   480
TCTGCTTCGG GCTCTGGGAG CCCAGAAGGA AGCCATCTCC CCTCCAGATG CGGCCTCAGC   540
TGCTCCACTC CGAACAATCA CTGCTGACAC TTTCCGCAAA CTCTTCCGAG TCTACTCCAA   600
TTTCCTCCGG GGAAAGCTGA AGCTGTACAC AGGGGAGGCC TGCAGGACAG GGACAGATG   660
ACCAGGTGTG TCCACCTGGG CATATCCACC ACCTCCCTCA CCAATATTGC TTGTGCCACA   720
CCCTCCCCCG CCACTCCTGA ACCCGTCGA GGGGCTCTCA GCTCAGCGCC AGCCTGTCCC   780
ATGGACCA
                                                                 788
```

FIGURE 5

```
  1 AAAAAGATGA GGTAATTGTG TTTTTATAAT TAAATATTTT ATAATTAAAA TATTTATAAT
    TTTTTCTACT CCATTAACAC AAAAATATTA ATTTATAAAA TATTAATTTT ATAAATATTA

61 TAAAATATTT ATAATTAAAT ATTTTATAAT TAAAATATTT ATAATTAAAT ATTTTATAAT
    ATTTTATAAA TATTAATTTA TAAAATATTA ATTTTATAAA TATTAATTTA TAAAATATTA

121 TAAAATATTT ATAATTAAAT ATTTTATAAT TAAAATATTT ATAATTAAAT ATTTTATAAT
    ATTTTATAAA TATTAATTTA TAAAATATTA ATTTTATAAA TATTAATTTA TAAAATATTA

181 TAAAATATTT ATAATTAAAT ATTTTATAAT TAAAATATTT ATAATTAAAT ATTTTATAAT
    ATTTTATAAA TATTAATTTA TAAAATATTA ATTTTATAAA TATTAATTTA TAAAATATTA

241 TAAAATATTT ATAATTAAAT ATTTTATAAT TAAAATGTTT ATAATTAAAT ATTTTATAAT
    ATTTTATAAA TATTAATTTA TAAAATATTA ATTTTACAAA TATTAATTTA TAAAATATTA

301 TAAAATGTTT ATAATTACAT ATTTTATAAT TAAAATGTTT ATAATTACAT ATTTTATAAT
    ATTTTACAAA TATTAATGTA TAAAATATTA ATTTTACAAA TATTAATGTA TAAAATATTA

361 TAAAATGTTT ATAATTACAT ATTTTATAAT TAAAATGTTT ATAATTACAT ATTTTATAAT
    ATTTTACAAA TATTAATGTA TAAAATATTA ATTTTACAAA TATTAATGTA TAAAATATTA

421 TAAAATGTTT ATAATTACAT ATTTTATAAT TACATATTTT ATAAAGTATT TATAATTACA
    ATTTTACAAA TATTAATGTA TAAAATATTA ATGTATAAAA TATTTCATAA ATATTAATGT

481 TATTTTATAA TTAAAGTATT TATAATTACA TATTTTATAA TTAAAGTATT TATAATTACA
    ATAAAATATT AATTTCATAA ATATTAATGT ATAAAATATT AATTTCATAA ATATTAATGT

541 TATTTTATAA TTCAATATTT TATAAATAGT TAAAAAGACG AGGAAAAAAT TAAAAAGACG
    ATAAAATATT AAGTTATAAA ATATTTATCA ATTTTCTGC TCCTTTTTTA ATTTTTCTGC

601 AGGTTATTGA TCTCAGGAAT TGTATTTGCC AAGTGAGAAG GAAAAAATAT TCACAAAGGC
    TCCAATAACT AGAGTCCTTA ACATAAACGG TTCACTCTTC CTTTTTTATA AGTGTTTCCG

661 TTGTA
    AACAT
```

FIGURE 6

```
   1 TCTAGACCCC AGTTTCTCTA TAAGATGAGA ATATTAGTCA CGATTTGGTT TCTAAGATCC
  61 TGTCTATGTT TGAGACTACA GATACCTGTT GCTACATTTC CCTTCATAGC TCTGAACAAG
 121 GAGAATTCAG CCCAATTCTC ATGGCCTTCT AAACAATCCA GAGTTTCAGT GCCATAAGGT
 181 ACTACAATTT AGTGTCAAAT TAAGTCAAAG GCTTCATTAG CCTGAAAGCT CTGTCCCTGG
 241 CCTGGGCATG GCAAACTGTA TCCCCACTG ACCATCCCCC TGTCTCCCTT CTCCCCAGAG
 301 ACTCCAGTAG CCTGGCGTCA TCACAGGGGC CAGACATATC CAACATGTTC CCAGCTTCCT
 361 GCCACTTGAC TTTCAGTGTG CCTCCCTCTT CAGTTACCCA AATCCTGCCC ACCATTCCAG
 421 AGCCAGTTCA ATCTCACCCA TCCAGGACCC CCGAGACCCC CATCGTACCA CTATAGTCTA
 481 ACTGTGGTGT AGACCCCACA CTGGGCACAT TGCGTACGCT CATTATTGGC TGTGACGTCT
 541 GATTATGCCC TTCTCCTGGT CTGGAAGCTC TCGGAGGTGC TCCATAATAC ATGAAGAGAA
 601 GTAGTGCTGG TGTGGGAATA GTGAGGTGTG TTTATCCATC CAGCTATCCG GCACCAGCAC
 661 TGGTCTCAGC TTTCTGAGGT AACACGTTCT GAGCCTTAGT CTTGAGAGAA CATAAAGAAA
 721 ACTTTTTTTA AAAGTAGTAA AAAGTGGCTG ACAAAAGCTG ACCAAAAGCC TTCAAAAGAA
 781 ATGCTAAGTT ATATCTAAGA AAGTTTACCC AAGGTCAGGC AAATATGAAA CCTAAAGCTA
 841 GACGTGGGGA AGAACTTCCG GAGAGTTGCA ATTCCCTGTG CCCCAGCATC CCCAGGAGGG
 901 CATGCCCACA TCTGATTTAG AAATCTGTGT AAAATGAGTG AAGGTTTCTA TTTCTTGGGC
 961 AGTGTGGGCA CAGGTCTTTG GAGAGGTCGA TGGCCTCCCA TAAAATCCTT CCTGCTTGAT
1021 GGTTCTGGAT CCTCAGCCAC AGCTCCTAAT AGCCATGAGG TTTGAGCCCA AAATAATTTA
1081 TGTGTTTGTT TTTTCAGCCC CAAAATTTCC ATAGAATCAA AGTAGTCAGA GCTGAATGGG
1141 GCTAAGAGAC CGTCCATTCC TGTCTTCTCA TCACAGATGA GGGACTGCCA CCCAGAGCCG
1201 TAGAAACTGT CCCATGGCCC CAGTTCCCAG ACCCTTCCTC TCTCCTACAG CTCCAAGTTC
1261 ACTGTGCATT CTAAATGAAG ATGTAAACAT AGGCAGCAAC ACTCAAGAGT AAAAATGAAG
1321 TGTGCATATG AAAGAAACCT ATTCACATGG ACCATATTAC ATTATAATCA CAGTGTTTAC
1381 TGCTTGACTA CCATCTGCCT GGGCTAGCAA GGGTGTCAGT GAGGAAGAGA GGACAAGGGG
1441 TACCAATCTG TGAACTACAC ATGGTTCTTG CTCTCCCAGC TTCTCTCTCC CATTGGCAAG
1501 GCAACAGGTA AACACATGAA AAATCAAATA ATGCTATAAG AGAAAAATGT ATTCAGGACA
1561 ACAACAGGTT TGTATGAAGG CCTTTCATCA TCGTTGTCCT ACCTAGAAAC TGAATGACAG
1621 GGAATCAGAG TCACAAGCTA TGAAGTCTAA CTGGGCTGGT CCCAGAGAAA GATTCAGTGC
1681 AGTAGGTGGG GCTGCAGCCA GCCCTGGGTG GGTGGAAGGA TGACATCCAC ATAGGCAAGA
1741 GGGTGATAAT TCACTTGCGC AGCTCCTCAC TGCACATTGA ACCCTGCTGA CTTCTGGCTT
1801 CTCTCCCGGG AGGAACTGCG ACTCAACATT CTGACCTTAT CTCTTGGGTA GCAGAATGAT
1861 GGAGAAGGAA AGTTTCTTTT TGCTTCTCGC AGGGGTTAAT CATCCATCTG GAATGCCTAC
1921 ATTTGGTTGA CAATGGCTCA CCCTATCATC TTCCTCCTGA ACCATTCACC TAAATGTGCC
1981 ATTTCTTTCC TGATAGTTCT CATTTGTGTG TGTGTGTGTG TGTGTGTGTG TGCACGTGCT
2041 CACACATGCA TGCTGTCACT GGGTAAACAG GCCACCCTGG GCACAGTTCC ATCTACAATG
2101 TTTGAAGTTT ACTTTCCAGC TTCTGGGCAT CATTTGCAAT TATAATGCTG TCACAGGCAG
2161 AAACGAGATA GGCTAATTAA TCGTTGTCAA TACTGATCCC TATTTGCCAG ATGAGATTTT
2221 GGAGCAGCAT GGCTGGGAAT AATTGGTATA GACTGTATTT CCTTGCTTTA TGTCACTGGA
2281 AATATTTATT TAAGCATCAC GGTCGCTATG CATAAATATC CTGGAAAATG GGGTATAGCT
2341 GAATGGTGCA GATTCATTCA TTCATATTCA GCAAATTATG TTCTAAGCAC CTACTTCAGT
2401 ACGTGAACAG CACTAAACTC AGAATATTGG TCTGCTGGGG TCCTTTATTA GCTTCCATGA
2461 TTCCCTGAAC TTGGCCAAGA CCCTTCTGGT CGGCTGCAGA TAGGCACAAT GGATAGTTTT
2521 GCTTCTAGA
```

RECOMBINANT DNA MOLECULES AND EXPRESSION VECTORS FOR ERYTHROPOIETIN

FIELD OF THE INVENTION

The invention relates to recombinant DNA molecules adapted for transfection of a host cell, and having a nucleic acid molecule encoding mammalian erythropoietin, operatively linked to an expression control sequence and having at least one SAR element. The invention also relates to expression vectors for transfection of a host cell and to host cells for expressing erythropoietin. The invention further relates to methods of preparing recombinant erythropoietin using the host cells transfected with the expression vectors.

BACKGROUND OF THE INVENTION

Erythropoietin (EPO) is a heavily glycosylated acidic glycoprotein with a molecular weight of approximately 35,000. The protein consists of 166 amino acids and has a leader signal sequence of 27 amino acids which is removed in vivo during secretion from the host cell. The sequence encoding the unprocessed EPO is 579 nucleotides in length (Jacobs et al, 1985, Lin et al, 1985, U.S. Pat. No. 4,703,008 and WO 86/03520).

Erythropoietin is the principal hormone involved in the regulation and maintenance of physiological levels of erythrocytes in mammalian circulation and functions to promote erythroid development, to initiate hemoglobin synthesis and to stimulate proliferation of immature erythroid precursors. The hormone is produced primarily by the adult kidney and foetal liver and is maintained in the circulation at concentrations of about 10–20 milliunits/ml of serum under normal physiological conditions. Elevated levels of EPO, induced by tissue hypoxia, trigger proliferation and differentiation of a population of receptive progenitor stem cells in the bone marrow, stimulating hemoglobin synthesis in maturing erythroid cells and accelerating the release of erythrocytes from the marrow into the circulation.

Recombinant EPO has been used to successfully treat patients, including patients having anemia as a result of chronic renal failure. As EPO is the primary regulator of red blood cell formation, it has applications in both the diagnosis and treatment of disorders of red blood cell production and has potential applications for treating a range of conditions.

The urine of severely anaemic patients was, at one time, almost the sole source for the commercial isolation of EPO. U.S. Pat. No. 3,033,753 describes a method for obtaining a crude EPO preparation from sheep plasma. The preparation of monoclonal antibodies specific for human EPO provided a means for identifying EPO produced from EPO mRNA, for screening libraries and for cloning the EPO gene. Human EPO cDNA has been cloned and expressed in *E. coli* (Lee-Huang, 1984, Proc. Natl. Acad. Sci. 81:2708). Isolation of the human EPO gene using mixtures of short or long synthetic nucleotides as probes led to the expression of biologically active EPO in mammalian cells (Lin, 1985, Proc. Natl. Acad. Sci. 82:7580; Lin, WO 85/02610; Jacobs, et al., 1985, Nature (Lond.) 313:806; Goto et al., 1988, Biotechnology 6:67). Jacobs, et al., 1985, supra, described the use of plasmids containing EPO DNA which were not integrated into the chromosomes of the COS host cells, but replicated autonomously in the cells to many thousands of copies, thereby killing the cells. Thus the expression of EPO was only a transient phenomenon in these cells.

Lin, in U.S. Pat. No. 4,703,008, reported expression of the human EPO gene in COS-1 and CHO cells. However, attempts to use transfected cells as production vehicles for EPO have been hampered by the low levels of EPO expressed by transfected cells. Given the important applications of recombinant EPO, there is much interest in developing more efficient methods for the expression of EPO.

Lin in U.S. Pat. No. 4,703,008 reported methods to increase the low amounts of EPO produced by transfected CHO cells (e.g. 2.99 u/ml/3 days) by a process of gene amplification. Levels of approximately 1500 units EPO/$10^6$ cells/48 hours were reported by Lin, following amplification. Gene amplification involves culturing cells in appropriate media conditions to select cells resistant to a selective agent, such as the drug methotrexate. Selection for cells resistant to methotrexate produces cells containing greater numbers of DHFR genes and passenger genes, such as the EPO gene carried on the expression vector along with the DHFR gene or transfected with the DHFR gene.

However, gene amplification is a very time consuming and labour intensive process. A major disadvantage of amplification is the inherent instability of amplified genes (McDonald, 1990, Crit. Rev. Biotech. 10:155). As it is usually necessary to maintain the amplified cells in the presence of toxic analogs to maintain high copy number, amplification may be inappropriate for large scale production due to the costs and toxicity of the selective agent. The high copy number of the DHFR-target transgene may also sequestor transcription factor, leading to a retardation of cell growth.

Genomic clones of human EPO have been used in attempts to develop stably transfected mammalian cell lines that secrete high levels of active erythropoietin (Powell, et al., 1986, Proc. Natl. Acad. Sci. 83:6465; Masatsuga, et al., European Patent Application Publication No. 0 236 059). In PCT Application WO 88/00241 Powell, describes the preparation of mammalian cell lines (COS-7 and BHK) transfected with the Apa I restriction fragment of the human EPO gene and selected for high expression by amplification.

Human EPO cDNA has also been expressed in mammalian cells (Yanagi, et al., 1989, DNA 8:419). Berstein, in PCT application WO 86/03520 describes the expression of EPO cDNA in various host cells, resulting in the secretion of up to 160 ng/ml of EPO into the medium after amplification. European Patent Application publication No. 0 267 678 discloses expression of recombinant EPO and secretion into the culture medium at levels of 600 units/ml.

A few scaffold attachment region (SAR) elements have been shown to increase the expression of reporter genes in transfected cells. SAR elements are thought to be DNA sequences which mediate attachment of chromatin loops to the nuclear matrix or scaffold. SAR elements are also known as MAR (matrix-associated regions) (reviewed by Phi-Van and Strätling, Prog. Mol. Subcell. Biol. 11:1–11, 1990). These elements will hereinafter be referred to as "SAR elements". SAR elements are usually 300 or more base pairs long, and they require a redundancy of sequence information and contain multiple sites of protein-DNA interaction. SAR elements are found in non-coding regions: in flanking regions or introns.

Stief, et al., (Nature 341:343–345, 1989) stably transfected chicken macrophage cells by constructs which contained the CAT gene either fused to the lysozyme promoter, or to the lysozyme promoter and the lysozyme enhancer. When the transcription units contained in both constructs were flanked on both sides by lysozyme 5' SAR elements (A elements), gene expression was increased about 10 times relative to transfectants, which contained the constructs lacking the SAR elements.

Phi-Van, et al., (Mol. Cell. Biol., 10:2302–2307, 1990) determined the influence of the SAR element located 5' to the chicken lysozyme gene (A element) on the CAT gene expression from a heterologous promoter (herpes simplex virus thymidine kinase promoter) in stably transfected heterologous cells (rat fibroblasts). The median CAT activity per copy number in transfectants was 10 times higher for the transcriptional unit flanked on both sides by A elements than for the transcriptional unit lacking SAR elements.

Klehr, et al., (Biochemistry, 30:1264–1270, 1991) stably transfected mouse L cells by different constructs containing the human interferon β gene. When the construct was flanked by SAR elements, the gene transcription level was enhanced 20–30 fold with respect to the SAR-free construct, containing only the immediate regulatory elements.

However, the above-noted experiments have been limited to a very few examples of SAR elements, expressing mostly reporter genes, such as chloramphenicol acetyl transferase (CAT) or luciferase. SAR elements have not shown consistent results in their effect on the expression of target genes and some target gene sequences have been found to inhibit the effect of SAR elements (Klehr, et al., 1991, Biochemistry 30:1264).

SUMMARY OF THE INVENTION

The present inventor has significantly found that SAR elements may be used to increase the expression of recombinant mammalian EPO DNA. The present inventor constructed expression vectors carrying EPO genomic or cDNA sequences flanked by 3' and 5' human apolipoprotein B SAR elements. The expression vectors, when transfected into host cells resulted in increased expression of EPO compared to control host cells transfected with EPO expression vectors lacking SAR elements. Host cells transfected with expression vectors carrying an EPO cDNA sequence flanked by 3' and 5' SAR elements which expressed high levels of EPO were selected and cloned to obtain homogenous stable cell lines over-expressing EPO. Cloning produced stable cell lines expressing high levels of EPO, without the need for amplification. SAR elements have not, to the inventor's knowledge, heretofore been used for long term expression of a target gene in stable cell lines, or for the expression of recombinant EPO.

The present invention thus provides a recombinant DNA molecule adapted for transfection of a host cell comprising a nucleic acid molecule encoding mammalian erythropoietin, an expression control sequence operatively linked thereto and at least one SAR element. In an embodiment, the nucleic acid molecule encodes mammalian erythropoietin having the amino acid sequence shown in SEQ ID NOS 33 or 34 and FIG. 3B. In another embodiment, the nucleic acid molecule has the sequence as shown in SEQ ID NO. 33 or 35.

The SAR element is preferably a SAR element co-mapping with the chromatin domain boundary, such as the human apolipoprotein SAR elements, most preferably the SAR element comprises the sequence as shown in SEQ ID NO. 36 or 37 and FIGS. 5 or 6.

The present invention also provides an expression vector comprising a recombinant DNA molecule adapted for transfection of a host cell comprising a nucleic acid molecule encoding mammalian erythropoietin, an expression control sequence operatively linked thereto and at least one SAR element.

In an embodiment, the expression vector comprises a nucleic acid molecule encoding erythropoietin and having the sequence shown in SEQ ID NO. 35 and FIG. 4 under the control of the human cytomegalovirus IE enhancer and promoter and the beta-globin intron and, flanked by 5' and 3' apolipoprotein SAR elements.

In a further embodiment, the expression vector comprises a nucleic acid molecule encoding erythropoietin and having the sequence shown in SEQ ID NO. 35 and FIG. 4, flanked by 5' and 3' apolipoprotein SAR elements under the control of elongation factor—1 alpha promoter and intron.

The present invention still further provides a mammalian cell stably transfected with the expression vector of the invention. The mammalian cell may be any mammalian cell, for example CHO-K1, BHK, Namalwa. An aspect of the invention provides a mammalian cell, lacking multiple copies of an amplified selectable marker gene and capable of expressing recombinant EPO in vitro at levels of at least 1,500, preferably over 2,000, most preferably from 2,000 to 10,000 u/$10^6$ cells in 24 hours.

In yet a further aspect, the invention provides a method of expressing recombinant mammalian erythropoietin comprising the steps of culturing a transfected mammalian cell of the invention in a suitable medium until sufficient amounts of erythropoietin are produced by the cell and separating the erythropoietin produced.

The present invention also relates to a method of preparing recombinant erythropoietin comprising transfecting a mammalian cell with an expression vector comprising a nucleic acid molecule encoding mammalian erythropoietin, an expression control sequence operatively linked thereto and at least one SAR element; culturing the transfected cell in a suitable medium until sufficient amounts of erythropoietin are produced by the cell and separating the erythropoietin produced. In a preferred embodiment, the erythropoietin is produced at levels of at least 2,000, most preferably form 2,000 to 10,000 u/$10^6$ cells in 24 hours in the absence of gene amplification. The invention also relates to erythropoietin produced by the method of the invention.

In an embodiment of the method, the mammalian cell is further transfected with a selectable marker gene and transfected cells are selected in conditions where the activity of the product encoded by the selectable marker gene is necessary for survival of the cells. In a preferred embodiment, the selectable marker gene is pSV2neo.

In a further embodiment, the method comprises the additional step of identifying and selecting cells producing high levels of erythropoietin; cloning the selected cells; establishing long term cell lines from the selected cells and; culturing the selected cells in a suitable medium until sufficient amounts of erythropoietin are produced by the cell and separating the erythropoietin produced.

The present invention further provides a transgenic non-human animal or embryo whose germ cells and somatic cells contain a DNA construct comprising the recombinant DNA molecule of the invention.

DESCRIPTION OF THE DRAWINGS

The invention will be better understood with reference to the drawings in which:

FIGS. 1B–D show the DNA sequences of the oligonucleotides synthesized to construct the erythropoietin gene;

FIG. 3A shows the DNA sequence of the erythropoietin gene; from 1–1860

FIG. 3B is a continuation of FIG. 3A showing the DNA sequence of the erythropoietin gene from 1861–3602;

FIG. 3C shows the amino acid sequence of the mature erythropoietin protein;

FIG. 4 shows the DNA sequence of the EPO$_{long}$ sequence;

FIG. 5 shows the DNA sequence of the 3' SAR element of human apolipoprotein B;

FIG. 6 shows the DNA sequence of Rh10;

DETAILED DESCRIPTION OF THE INVENTION

Figure 1A:
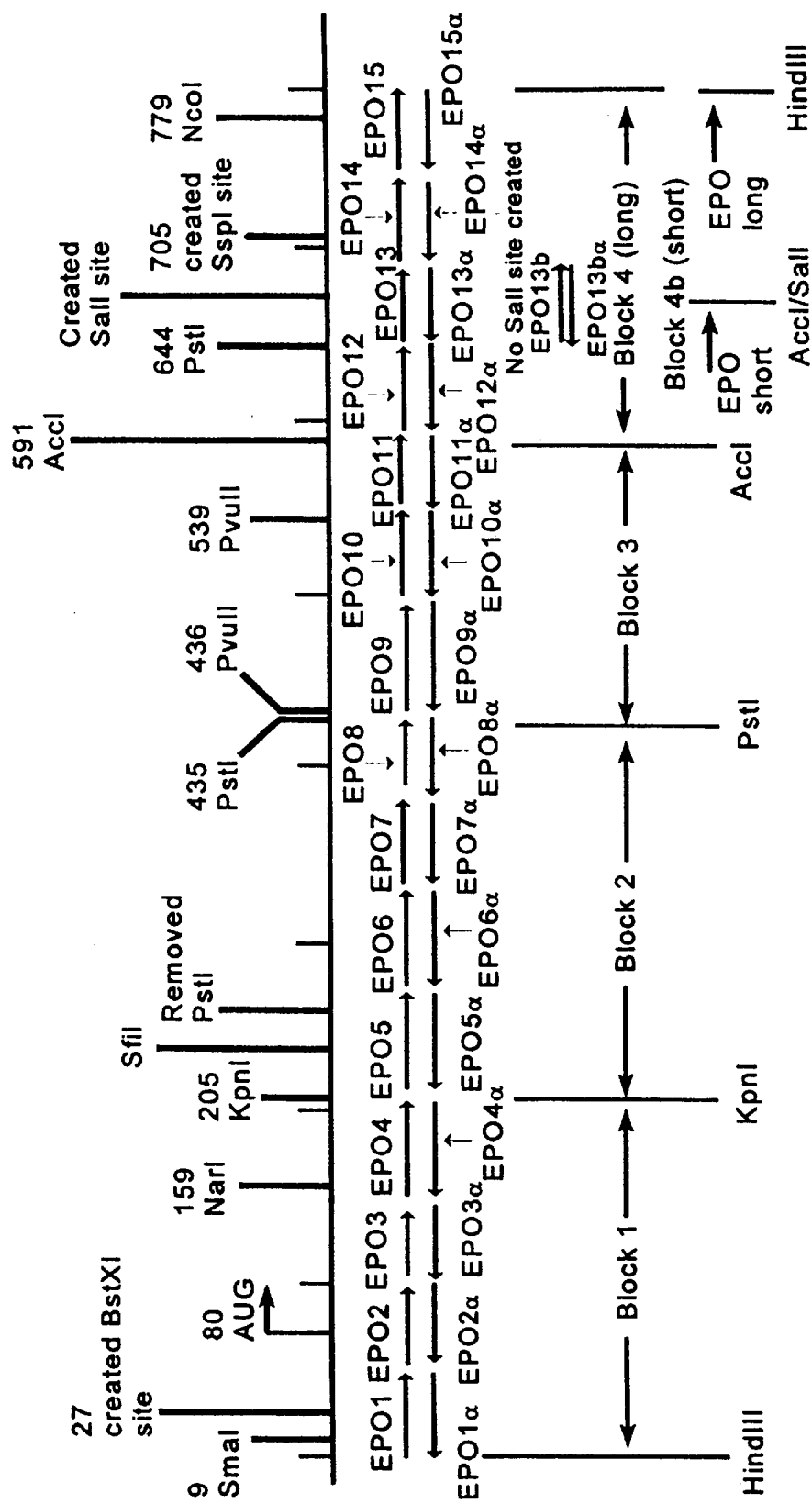
FIG. 1A is a schematic representation of the procedure for synthesizing the erythropoietin gene.

As hereinbefore noted, the present inventor has significantly found that recombinant EPO expression is increased in host cells transfected with recombinant DNA encoding EPO operatively linked to an expression control sequence and SAR elements, compared to host cells transfected with EPO in the absence of SAR elements.

The present invention thus provides a recombinant DNA molecule adapted for transfection of a host cell comprising a nucleic acid molecule encoding mammalian erythropoietin, an expression control sequence operatively linked thereto and at least one SAR element. In a preferred embodiment the EPO is human EPO and in a particularly preferred embodiment the nucleic acid molecule has a sequence which encodes erythropoietin having the amino acid sequence as shown in SEQ ID NO 33 and 34 and FIG. 3C. In a particular embodiment, the nucleic acid molecule has the sequence as shown in SEQ ID NOS. 35 or 33.

1. Nucleic Acid Molecules Encoding Erythropoietin

The term "a nucleic acid molecule encoding mammalian EPO" as used herein means any nucleic acid molecule which encodes biologically active EPO. It will be appreciated that, within the context of the present invention, EPO may include various structural forms of the primary protein which retain biological activity. Biologically active EPO will include analogues of EPO having altered activity, for example having greater biological activity than EPO. Biological activity of EPO may be readily determined by the methods referred to herein.

Nucleic acid molecules encoding EPO include any sequence of nucleic acids which encode biologically active EPO, preferably, the nucleic acid molecule also encodes the leader sequence of the prepeptide to permit secretion of EPO from a cell transfected with the recombinant DNA molecule of the invention. The amino acid sequence of the leader sequence of the prepeptide is shown in SEQ ID NO. 33, from amino acid number −27 to −1. In an embodiment, the nucleic acid molecule encodes a peptide having the amino acid sequence as shown in SEQ ID NO. 33 and 34 and FIG. 3C. Nucleic acid molecules encoding EPO include the entire EPO gene sequence as shown in SEQ ID NO. 33, one or more fragments of this sequence encoding the EPO prepeptide (nucleotides 625–637, 1201–1346, 1605–1691, 2303–2482 and 2617–2772 in SEQ ID NO. 33) or the mature EPO peptide (nucleotides 1269–1346, 1605–1691, 2303–2482 and 2617–2769 in SEQ ID NO. 33) or nucleic acid molecules having substantial homology thereto, or any fragment thereof encoding biologically active EPO, such as the EPO$_{Long}$ sequence shown in SEQ ID NO. 35 and FIG. 4.

It will be appreciated that the invention includes nucleotide or amino acid sequences which have substantial sequence homology with the nucleotide and amino acid sequences shown in SEQ ID NOS: 33, 34 and 35 and FIGS. 3A, 3B, 3C and 4. The term "sequences having substantial sequence homology" means those nucleotide or amino acid sequences which have slight or inconsequential sequence variations from the sequences disclosed in SEQ ID NOS. 33, 34 and 35 i.e. the homologous sequences function in substantially the same manner to produce substantially the same polypeptides as the actual sequences. Due to code degeneracy, for example, there may be considerable variation in nucleotide sequences encoding the same amino acid sequence. The variations may be attributable to local mutations or structural modifications.

It will also be appreciated that a double stranded nucleotide sequence comprising a DNA segment of the invention or an oligonucleotide fragment thereof, hydrogen bonded to a complementary nucleotide base sequence, and an RNA made by transcription of this double stranded nucleotide sequence, are contemplated within the scope of the invention.

A number of unique restriction sequences for restriction enzymes are incorporated in the DNA sequence identified in SEQ ID NO: 33, and 35 and in FIGS. 3A and 3B, and 4 respectively, and these provide access to nucleotide sequences which code for polypeptides unique to EPO. DNA sequences unique to EPO or isoforms thereof, can also be constructed by chemical synthesis and enzymatic ligation reactions carried out by procedures known in the art.

Mutations may be introduced at particular loci for instance by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific mutagenesis procedures may be employed to provide an altered gene having particular codons altered according to the substitution, deletion, or insertion required. Deletion or truncation derivatives of EPO may also be constructed by utilizing convenient restriction endonuclease sites adjacent to the desired deletion. Subsequent to restriction, overhangs may be filled in or removed, and the DNA religated. Exemplary methods of making the alterations set forth above are disclosed by Sambrook et al. (Molecular cloning A Laboratory Manual, 2d Ed., Cold Spring Harbor Laboratory Press, 1989).

The scope of the present invention also includes conjugates of EPO along with other molecules such as proteins or polypeptides. This may be accomplished, for example, by the synthesis of N-terminal or C-terminal fusion proteins or fragments of proteins to facilitate purification or identification of EPO (see U.S. Pat. No. 4,851,341, see also, Hopp et al., Bio/Technology 6:1204, 1988.) Thus, fusion proteins may be prepared by fusing through recombinant techniques the N-terminal or C-terminal of EPO or other portions thereof, and the sequence of a selected protein with a desired biological function. The resultant fusion proteins contain EPO or a portion thereof fused to the selected protein or portion thereof. Examples of proteins which may be selected to prepare fusion proteins include lymphokines such as gamma interferon, tumor necrosis factor, IL-1, IL-2,IL-3, IL-4, IL-5, IL-6, IL-7, IL-8, IL-9, IL-10, IL-11, GM-CSF, CSF-1 and G-CSF, nerve growth factor, protein A, protein G, GST and the Fc portion of immunoglobulin molecules.

Nucleic acid molecules encoding EPO may be chemically synthesized or may be cloned from a genomic or cDNA mammalian library using oligonucleotide probes derived from the known EPO sequences following standard procedures. In this manner, nucleic acid molecules encoding EPO may be obtained from the cells of a selected mammal.

For example, cDNA sequences encoding mammalian EPO may be isolated by constructing cDNA libraries derived from reverse transcription of mRNA in cells from the selected mammal which express EPO, for example adult kidney cells or foetal liver cells. Increased levels of expression in the cell may also be achieved, for example by inducing anemia in the mammal. DNA oligonucleotide probes may be used to screen the library for positive clones. Genomic DNA libraries may also be constructed and screened by plaque hybridization using fragments of EPO cDNA as probes.

Nucleic acid molecules which encode EPO may also be obtained from a variety of sources, including for example, depositories which contain plasmids encoding EPO sequences including the American Type Culture Collection (ATCC, Rockville Md.), and the British Biotechnology Limited (Cowley, Oxford England). EPO DNA as described in Lin, (1985, Proc. Natl. Acad. Sci. U.S.A. 82:7580) is deposited as HUMERPA, Accession No M11319.

Various post translational modifications are contemplated to the EPO encoded by the nucleic acid molecule. For example, EPO may be in the form of acidic or basic salts, or in neutral form. In addition, individual amino acid residues may be modified by, for example, oxidation or reduction. Furthermore, various substitutions, deletions, or additions may be made to the amino acid or DNA nucleic acid sequences, the net effect of which is to retain biological activity of EPO.

In a preferred embodiment of the invention, the nucleic acid molecule of the invention comprises the $EPO_{Long}$ nucleotide molecule encoding EPO, shown in SEQ ID NO. 35 and FIG. 4. $EPO_{Long}$ may be chemically synthesized by assembling short nucleotides, for example, as shown in FIG. 1B and SEQ ID NOS. 1 to 32. The procedure for the synthesis and assembly of the $EPO_{Long}$ sequence from the short nucleotides is shown schematically in FIG. 2B.

2. SAR Elements

The term "SAR elements" as used herein refers to DNA sequences having an affinity or intrinsic binding ability for the nuclear scaffold or matrix. SAR elements are usually 300 or more base pairs long, require a redundancy of sequence information and contain multiple sites of protein-DNA interaction. Preferably SAR elements are found in non coding regions: in flanking regions or introns.

Suitable SAR elements for use in the invention are those SAR elements which promote elevated and position-independent gene activity in stable transfectants. SAR elements may be obtained, for example, from eukaryotes including mammals, plants, insects and yeast, preferably mammals. SAR elements are preferably selected which co-map with the boundaries of a chromatin domain. SAR elements co-mapping with the chromatin domain boundary are preferred for the recombinant DNA molecules of the invention to promote the formation of an independent domain containing the nucleic acid molecule encoding mammalian EPO to be expressed in stable transfectants.

Examples of preferred SAR elements which co-map with the chromatin domain boundary include the following: the 5' human apoB SAR element (Rh10), a XbaI fragment spanning nucleotides −5,262 to −2,735 of the human apoB gene, as shown in SEQ ID 37 and FIG. 6 and as described in Levy-Wilson and Fortier, 1989, (J. Biol. Chem. 264:21196). This region actually contains two SAR elements, a proximal and distal one. It is contemplated that either the proximal and distal SAR elements together or the distal element alone may be used. The 3' human apoB SAR element extends between nucleotides +43,186 and +43,850. The DNA sequence of this 665 bp region is described in Levy-Wilson and Fortier, 1989, supra and shown in SEQ ID NO. 36 and FIG. 5. A 60-bp deleted 3'human apoB SAR element (Rh32), is also suitable for use in the invention. The deletion is shown within brackets in FIG. 5.

Examples of suitable protocols for identifying SAR elements for use in the present invention are described below. The high salt method may be used to identify SAR elements by measuring the ability of labelled naked DNA fragments to bind nuclear matrices in the presence of unlabelled competitor DNA, typically *E. coli* DNA. DNA fragments bound to nuclear matrices under these conditions are operationally defined as SAR elements. The nuclear matrices may be isolated by the 2M NaCl extraction of DNAase I-digested nuclei (Cockerill and Garrard, 1986, Cell 44, 273–282). Chromosomal loop anchorage of the kappa immunoglobulin gene occurs next to the enhancer in a region containing topoisomerase II sites. (Cockerill, 1990, Nucleic. Acids. Res. 18, 2643–2648).

In the low salt method for identifying SAR elements nuclei are heated to 37° C. and then extracted with a buffer containing 25 mM 3,5-diiodosalicylic acid lithium salt (LIS) which removes histones. The LIS-treated nuclei are extracted several times with a low salt buffer. The extracted nuclei are digested with restriction endonucleases. The solubilized (non-matrix bound) DNA fragments are removed by centrifugation. Southern blot hybridization with labelled probes identifies the DNA fragments bound to the nuclear matrix (Mirkovitch et al., 1984, Cell 39, 223–232). Both the above-noted methods yield essentially the same result, that is, a sequence identified as a SAR element with the high salt method will also be identified as a SAR element by the Lis-low salt method.

The SAR element may be inserted into the recombinant molecule of the invention upstream or downstream from the nucleic acid molecule encoding EPO and the operatively linked expression control sequence. Preferably, the SAR element is inserted within 0.1 to 100 kb upstream or downstream, more preferably from 0.1 to 50 kb, most preferably 0.5 to 10. In a preferred embodiment, more than one SAR element should be inserted into the recombinant molecule of the invention, preferably the SAR elements should be located in flanking positions both upstream and downstream from the nucleic acid molecule encoding EPO and the operatively linked expression control sequence. The use of flanking SAR elements in the nucleic acid molecules may allow the SAR elements to form an independent loop or chromatin domain, which is insulated from the effects of neighbouring chromatin. Accordingly, EPO gene expression may be position-independent and the level of expression should be directly proportional to the number of integrated copies of the recombinant DNA molecules of the invention. Preferably, the SAR elements should be inserted in non-coding regions of the recombinant DNA molecule.

The recombinant DNA molecules of the invention may be advantageously used to express elevated levels of mammalian EPO. Routine procedures may be employed to confirm that the SAR elements selected by the above-noted protocols are useful for expressing elevated levels of mammalian EPO. For example, appropriate expression vectors comprising a nucleic acid molecule encoding mammalian erythropoietin and an expression control sequence operatively linked thereto may be constructed with and without (control vectors) SAR elements. Mammalian host cells may be stably transfected with an EPO expression vector having a selectable marker gene or may be stably co-transfected with an EPO expression vector and a selectable marker gene vector, such as a pSV2-neo vector (which carries the gene conferring the resistance to the antibiotic G-418). The levels of EPO secreted may be determined, for example, by RIA and the effect of the flanking SAR elements on EPO production may be determined. Transfected cell populations producing the highest levels of EPO as detected by RIA, may be selected and subjected to successive rounds of cloning by the dilution method.

3. Expression Control Sequences

Suitable expression control sequences may be derived from a variety of mammalian sources. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, splice signals, polyadenylation signals, including a translation initiation signal. Additionally, depending on the host cell chosen and the vector employed, other genetic elements, such as an origin of replication, additional DNA restriction sites, enhancers, sequences conferring inducibility of transcription, and selectable markers, may be incorporated into the expression vector.

Strong promoters (or enhancer/promoters) are preferably selected. A strong promoter is one which will direct the transcription of a gene whose product is abundant in the cell. The relative strength and specificities of a promoter/enhancer may be compared in comparative transient transfection assays. In an embodiment, a promoter may be selected which has little cell-type or species preference and which can therefore be strong when transfected into a variety of cell types.

In preferred embodiments of the invention, the EF1 promoter or the human cytomegalovirus. (HCMV) IE (immediate-early) enhancer and promoter may be used. The human EF-1α gene promoter is stronger than the adenovirus major late promoter in a cell free system (Uetsuki et al., 1989, J. Biol. Chem. 264:5791). The EF1 promoter is the promoter for the human chromosomal gene for the polypeptide chain elongation factor-1α: extending from −303 to −1 for genomic constructs and from −303 to +986 for cDNA constructs. For the cDNA constructs, the EF1 DNA sequence includes the promoter as well as exon 1 and intron 1 (Uetsuki et al, 1989, J. Biol. Chem. 264, 5791–5798). The human cytomegalovirus (hCMV) IE (immediate-early) enhancer and promoter, extend from −598 to +54 in the sequence (Kay and Humphries, 1991, Methods in Molecular and Cellular Biology 2, 254–265).

4. Methods of Expressing EPO

As hereinbefore noted, the present invention also provides expression vectors which include the recombinant DNA molecule of the invention and mammalian cells stably transfected with the expression vector.

Suitable expression vectors, such as plasmids, bacteriophage, retroviruses and cosmids are known in the art. Many plasmids suitable for transfecting host cells are well known in the art, including among others, pBR322 (see Bolivar et al., Gene 2:9S, 1977), the pUC plasmids pUC18, pUC19, pUC118, pUC119 (see Messing, Meth in Enzymology 101:20–77, 1983 and Vieira and Messing, Gene 19:259–268, 1982), and pNH8A, pNH16a, pNH18a, and Bluescript M13 (Stratagene, La Jolla, Calif.). Retroviral vectors are reviewed in Eglitis and Anderson, 1988, Biotechniques 6:608. Suitable expression vectors are those which are stably incorporated into the chromosome of the mammalian host cell.

The recombinant DNA molecule of the invention may be expressed by a wide variety of mammalian cells. Methods for transfecting such cells to express foreign DNA are well known in the art (see, e.g., Itakura et al., U.S. Pat. No. 4,704,362; Hinnen et al., PNAS USA 75:1929–1933, 1978; Murray et al., U.S. Pat. No. 4,801,542;

Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. Molecular Cloning A Laboratory Manual, 2nd edition, Cold Spring Harbor Laboratory Press, 1989, all of which are incorporated herein by reference). Suitable expression vectors include vectors having a selectable marker gene.

Mammalian cells suitable for carrying out the present invention include, among others: COS (e.g., ATCC No. CRL 1650 or 1651), BHK (e.g., ATCC No. CRL 6281), CHO-K1 (ATCC No. CCL 61), HeLa (e.g., ATCC No. CCL 2), 293 (ATCC No. 1573) and NS-1 cells. As noted above, suitable expression vectors for directing expression in mammalian cells generally include a promoter, as well as other transcriptional and translational control sequences. Common promoters include SV40, MMTV, metallothionein-1, adenovirus Ela, CMV, immediate early, immunoglobulin heavy chain promoter and enhancer, human cytomegalovirus 1E enhancer and promoter and RSV-LTR. Protocols for the transfection of mammalian cells are well known to those of ordinary skill in the art. Representative methods include calcium phosphate mediated gene transfer, electroporation, retroviral, and protoplast fusion-mediated transfection (see Sambrook et al., supra).

Given the teachings provided herein, promoters, terminators, and methods for introducing expression vectors of an appropriate type into mammalian calls may be readily accomplished. Accordingly, the invention also relates to mammalian cells stably transfected with an expression vector of the invention. The term "stably transfected" refers to the fact that suitable expression vectors are those which stably incorporate the recombinant DNA molecule of the invention into the chromosomes of the mammalian cell.

The invention also relates to a mammalian cell lacking a selectable marker gene capable of being amplified and, capable of expressing recombinant EPO in vitro at levels of at least 1,500, preferably at least 2,000, most preferably 2,000 to 10,000 u/$10^6$ cells in 24 hours.

In an embodiment, the invention also relates to a mammalian cell, having less than 1,000, preferably less than 100, most preferably less than 10 copies of a selectable marker gene and capable of expressing recombinant EPO in vitro at levels of at least 1,500, preferably at least 2,000, most preferably 2,000 to 10,000 u/$10^6$ cells in 24 hours.

Amplification refers, for example, to the process of culturing cells in appropriate medium conditions to select cells resistant to the drug methotrexate. Such cells have been found to be resistant to methotrexate due to an amplification of the number of their gene encoding dihydrofolate reductase (DHFR). Selection for cells resistant to methotrexate produces cells containing greater numbers of DHFR genes. Passenger genes, such as the EPO gene carried on the expression vector along with the DHFR gene or co-transfected with the DHFR gene may also be increased in their gene copy number. Cells which have been amplified thus have multiple copies of the selectable marker gene in addition to the passenger gene.

It is an advantage of the present invention that high levels of EPO expression may be achieved without the need for amplification. Thus the mammalian cells of the invention express high levels of EPO and do not express high levels of a selectable marker gene. The expression of high levels of selectable marker genes in amplified cells may interfere with the cell's ability to remain stable in long term culture and to express high levels of EPO in long term culture. Amplified cells may carry certain disadvantages such as non-specific toxicity associated with exposure of the cells to the inhibitory drug or compound.

Selectable marker genes which may be amplified in a mammalian host cell are known in the art and include the genes encoding proteins conferring resistance to chloramphenicol (Wood et al., CSHSQB 51:1027, 1986), methotrexate (Miller, MC Biol., 5:431, 1985; Corey et al., Blood 75:337, 1990; Williams et al., Proc. Natl. Acad. Sci. USA, 83:2566, 1986; Stead et al., Blood 71:742, 1988), mycophenolic acid (Stuhlmann et al., Proc. Natl. Acad. Sci. USA 81:7151, 1984), or various chemotherapeutic agents (Guild et al., Proc. Natl. Acad. Sci USA 85:1595, 1988; Kane et al., Gene 84:439, 1989; Choi et al., Proc. Natl. Acad. Sci. USA; Sorrentino, et al., Science 257:99, 1992). A discussion of selectable marker genes, including those capable of being amplified is provided in Kreigler, 1990, "Gene Transfer and Expression, A Laboratory Manual", Chapter 6, Stockton Press, and include the gene encoding dihydrofolate reductase.

Within another aspect, the present invention relates to a method of preparing recombinant erythropoietin comprising transfecting a mammalian cell with an expression vector comprising a nucleic acid molecule encoding mammalian erythropoietin, an expression control sequence operatively linked thereto and at least one SAR element; culturing the transfected cell in a suitable medium until sufficient amounts of erythropoietin are produced by the cell and separating the erythropoietin produced. In an embodiment, the mammalian cell may be further transfected with a selectable marker gene and the transfected cells may be selected by means of the selectable marker gene. Examples of selectable marker genes are given above and include neo.

In an embodiment of the method, cells producing high levels of erythropoietin may be identified and selected and subcloned to establish long term cell lines from the selected cells and; the selected cells may be cultured in a suitable medium until sufficient amounts of erythropoietin are produced by the cell. EPO produced may then be separated from the medium.

It is an advantage of the method of the invention that cell lines may be established which are stable over the long term, at least six months. The long term cell lines of the invention express consistently high levels of EPO and may be maintained without the selective pressure often required to maintain the high copy number of amplified genes in cell lines which have been subjected to amplification.

EPO may be prepared by culturing the host/vector systems described above, in order to express the EPO. Recombinantly produced EPO may be further separated and further purified as described in more detail below.

Biologically active EPO expressed may be assayed by known procedures such as tritiated thymidine uptake by mouse spleen cell erythrocyte precursors (Krystal, et al., 1986, Blood 67:71); the exhypoxic mouse method using $^{59}$Fe incorporation into erythrocyte precursors (Cotes and Bangham, 1961, Nature 191:1065); $^{59}$Fe uptake into fetal mouse liver cells (Dunn et al, 1975, Exp. Hematol. 3:65); and the starved rat method (Goldwasser and Gross, 1975, Methods Enzymol. 37:109). EPO once expressed may also be quantitated, for example by RIA, separated and purified by known techniques such as ultrafiltration, flat-bed electrofocusing, gel filtration, electrophoresis, isotachophoresis and various forms of chromatography, such as ion exchange, adsorption chromatography, column electrophoresis and various forms of HPLC. Procedures for the chromatographic separation of EPO are described, for example in U.S. Pat. No 4,667,016.

The present invention also relates to transgenic non-human mammals or embryos whose germ cells and somatic cells contain a DNA construct comprising the recombinant DNA molecule of the invention. The recombinant DNA molecule of the invention may be expressed in non-human transgenic animals such as mice, rats, rabbits, sheep, cows and pigs (see Hammer et al. (Nature 315:680–683, 1985), Palmiter et al. (Science 222:809–814, 1983), Brinster et al. (Proc Natl. Acad. Sci USA 82:44384442, 1985), Palmiter and Brinster (Cell. 41:343–345, 1985) and U.S. Pat. No. 4,736,866). Briefly, an expression unit, including a DNA sequence to be expressed together with appropriately positioned expression control sequences, is introduced into pronuclei of fertilized eggs. Introduction of DNA is commonly done by microinjection. Integration of the injected DNA is detected by blot analysis of DNA from tissue samples, typically samples of tail tissue. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., 1983, ibid), which allows regulated expression of the transgene. Alternatively, yeast artificial chromosomes (YACs) may be utilized to introduce DNA into embryo-derived stem cells by fusion with yeast spheroblasts carrying the YAC (see Capecchi, Nature 362:255–258, 1993; Jakobovits et al., Nature 362:255–258, 1993). Utilizing such methods, animals may be developed which express EPO in tissues. Tissue specific promoters may be used to target expression of EPO in cells. Tissue specific promoters include the 5' or 3' flanking sequences of the beta-globin, elastase, alpha-fetoprotein, alpha-A crystalline, an erythroid specific transcriptional element and insulin genes (Yee, et al. (1989) P.N.A.S., U.S.A. 86, 5873–5877; Swift, et al. 1984, Cell 38:639; Storb et al., Nature (Lond.) 310:238; Grosscheldl et al., 1985 Cell 41:885; Shani, 1985 Nature (Lond) 314:238 and Chada et al, 1985, Nature (Lond)). The use of SAR elements in the development of transgenic animals is described for example in Xu, 1989, J. Biol. Chem. 264:21190; McKnight et al., 1992, Proc. Natl. Acad. Sci. U.S.A. 89:6943; Brooks, et al., 1994, Mol. Cell. Biol. 14:2243 and; Forrester, et al., 1994, Science 265:1221.

In a preferred embodiment suitable promoters and/or enhancers may be selected from mammary gland specific genes which are normally only expressed in milk, for example the genes encoding α-casein (Gene Pharming, Leiden, Netherlands), β-casein (Genzyme Transgenics Corp. Framingham, Mass.), γcasein, κ-casein α-lactablbumin β-lactalbumin β-lactogloblin (PPL Therapeutics Ltd, Edinburgh, Scotland) and whey acidic protein (Altra Bio Inc., Arden Hills Minn.). Methods for targeting recombinant gene expression to the mammary gland of a mammal are described, for example, in U.S. Pat. No. 5,304, 489. Briefly, a DNA construct with the recombinant DNA molecule of the invention comprising a mammary gland specific promoter may be microinjected into a newly fertilized egg leading to integration of the construct into the genome and secretion of the protein into the milk of a mature lactating female. EPO expressed in the milk may be purified from the milk using standard procedures after skimming off the milk fat, separating out the caseins and precipitating EPO out of the whey fraction, followed by standard protein purification procedures for EPO as described elsewhere herein.

A major problem in the generation of transgenic mammals for the expression of recombinant proteins has been the varying levels of expression which result due to chromosomal factors in the local environment where the construct integrates, for example regulatory elements and the state of the chromatin (open or closed). As a result, generating a transgenic mammal that produces high levels of a recombinant protein has been achieved only by laborious trial and error.

The present invention provides a transgenic non-human animal whose germ cells and somatic cells contain a DNA construct comprising the recombinant DNA molecules of the invention, comprising a tissue specific promoter, preferably the tissue specific promoter is a promoter which specifically expresses EPO in milk. In a particularly preferred embodiment, the recombinant molecule contained in the transgenic non-human mammal comprises the nucleic acid molecule encoding EPO and the expression control sequence operatively linked thereto, flanked by SAR elements. An advantage of DNA constructs having flanking SAR elements is that expression of EPO may be independent of the site of integration of the construct as the construct is insulated from surrounding chromosome material by the SAR elements, which define an open chromatin domain.

5. Applications

It will be apparent that the recombinant DNA molecules, expression vectors, transfected host cells, methods and transgenic animals of the invention will be useful for the efficient expression and production of recombinant mammalian EPO in vitro and in vivo as described above.

Recombinant EPO may be used to treat animals and human patients, including patients having anemia as a result of chronic renal failure. As EPO is the primary regulator of red blood cell formation, it has applications in both the diagnosis and treatment of disorders of red blood cell production and has potential applications for treating a range of conditions such as anemia, sickle cell disease, conditions where red cells are depleted (for example in bone marrow transplants), thalassemia, cystic fibrosis, menstrual disorders, acute blood loss and conditions involving abnormal erythropoiesis (for example cancers of the haemopoietic system), conditions involving destruction of red blood cells by over exposure to radiation, reduction in oxygen intake at high altitudes, complications or disorders secondary to AIDS and prolonged unconsciousness.

The recombinant DNA molecules, expression vectors and transformed mammalian cells of the invention will also have useful applications in gene therapy, whereby a functional EPO gene is introduced into a mammal in need thereof, for example mammals having anemias. The transfer of the recombinant DNA molecule of the invention into mammalian cells may be used, for example in gene therapy to correct an inherited or acquired disorder through the synthesis of missing or defective EPO gene products in vivo.

The recombinant DNA molecule of the invention may be used in gene therapy as briefly described below. The recombinant DNA molecule may be introduced into cells of a mammal, for example haemopoietic stem cells removed from the bone marrow or blood of the mammal. Hemopoietic stem cells are particularly suited to somatic gene therapy as regenerative bone marrow cells may be readily isolated, modified by gene transfer and transplanted into an immunocompromised host to reconstitute the host's hemopoietic system. Suitable hemopoietic stem cells include primitive hemopoietic stem cells capable of initiating long term culture (Sutherland et al., Blood, Vol. 74, p. 1563, 1986 and Udomsakdi et al., Exp. Hematol., Vol. 19, p. 338, 1991.) Suitable cells also include fibroblasts and hepatocytes.

The recombinant DNA molecules of the invention may be introduced into the cells by known methods, including calcium phosphate mediated transfection described herein or retroviral mediated uptake. The recombinant DNA molecule of the invention may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. The recombinant DNA molecules of the invention may also be applied extracellularly such as by direct injection into cells. Freed et al., New Eng. J. Med. 327(22):1549–1555, 1992, describe a method for injecting fetal cells into brains of Parkinson's patients. Gene therapy involving bone marrow transplant with recombinant primary hemopoietic stem cells requires efficient gene transfer into the stem cells. As a very small number of primary stem cells can reconstitute the entire host hemopoietic system it is important that the transferred gene be efficiently expressed in the recombinant stem cells transferred. Thus it is expected that the recombinant molecules of the invention will be particularly advantageous for use in gene therapy to correct defects in the erythropoietin gene.

As hereinbefore noted, the recombinant DNA molecules of the invention, having flanking SAR elements, are particularly useful for the expression of EPO in transgenic mammals and therefore they are particularly useful in gene therapy as the SAR elements define an open chromatin domain and insulate the construct from the surrounding chromosome material, thereby, providing position-independent expression.

The following non-limiting examples are illustrative of the present invention:

EXAMPLES

Example 1

Synthesis of EPO cDNA Sequences

EPO Oligonucleotide synthesis

EPO oligonucleotides were synthesized with the Applied Biosystems Inc. 392 DNA/RNA Synthesizer at the 0.2 $\mu$m scale (~500 $\mu$g). Oligonucleotide 5' ends were phosphorylated, except for the ones coinciding with the 5' ends of each of the four blocks. Oligonucleotides lacking 5' phosphorylation were purified using the Applied Biosystems Oligo Purification Cartridge (OPC). Oligonucleotides with 5' phosphorylation were purified from acrylamide gels (according to the protocol described in Sambrook, Fritsch, and Maniatis, 1989. Molecular Cloning: A Laboratory Manual, 2nd Edition. Cold Spring Harbor Laboratory Press, pp. 11.23 –11.30). $C_{18}$ Sep-Pak cartridges from Millipore were used to remove salts. All oligos were resuspended in double distilled $H_2O$.

Oligonucleotides EPO1 (SEQ ID NO. 1), EPO2 (SEQ ID NO. 2), EPO3 (SEQ ID NO. 3), EPO4 (SEQ ID NO. 4), EPO5 (SEQ ID NO. 5), EPO6 (SEQ ID NO. 6), EPO7 (SEQ ID NO. 7), EPO8 (SEQ ID NO. 8), EPO9 (SEQ ID NO. 9), EPO10 (SEQ ID NO. 10), EPO11 (SEQ ID NO. 11), EPO12 (SEQ ID NO. 12), EPO13 (SEQ ID NO. 13), EPO13b (SEQ ID NO. 14), EPO14 (SEQ ID NO. 15), EPO15 (SEQ ID NO. 16), EPO1α (SEQ ID NO. 17), EPO2α (SEQ ID NO. 18), EPO3α (SEQ ID NO. 19), EPO4α (SEQ ID NO. 20), EPO5α (SEQ ID NO. 21), EPO6α (SEQ ID NO. 22), EPO7α (SEQ ID NO. 23), EPO8α (SEQ ID NO. 24), EPO9α (SEQ ID NO. 25), EPO10α (SEQ ID NO. 26), EPO11α (SEQ ID NO. 27), EPO12α (SEQ ID NO. 28), EPO13α (SEQ ID NO. 29), EPO13Bα (SEQ ID NO. 30) EPO14α (SEQ ID NO. 31) and EPO15α (SEQ ID NO. 32) as shown in FIGS. 1B, 1C and 1D were synthesized. All oligonucleotides labelled with "α" are for the complementary strand (i.e. negative sense of the EPO gene). Oligonucleotides EPO1 (SEQ ID NO. 1), EPO1α (SEQ ID NO. 17), EPO15 (SEQ ID NO. 16) and EPO15α (SEQ ID NO. 32) contain extra bases at their 5'-ends and 3'ends, respectively, which facilitate construction of a HindIII recognition site.

Assembly of blocks 1, 2, 3 and 4

Blocks 1, 2, 3, and 4 as shown in FIG. 1A were synthesized by ligating the above-noted EPO oligonucleotides according to the following protocol.

40 pmoles of each oligonucleotide were mixed in a microcentrifuge tube in a final volume of 50 μl. The oligonucleotides were annealed by heating at 98° C. for 5 minutes in a heat block. The heat block containing the tube was removed from the heating unit and allowed to cool on the benchtop to 30° C. (approximately 1.5 hrs). 6 μl of 10×T$_4$ DNA ligase buffer (0.5M Tris-HCl, pH 7.8, 0.1M MgCl$_2$, 0.1M DTT, 10 mM ATP and 250 μg/ml BSA), was added to 2 μl (or 2 units) of T$_4$ DNA ligase, and brought to volume to 60 μl with double distilled H$_2$O and incubated overnight at 14° C. The mixture was heated at 75° C. for 10 minutes to inactive ligase and then cooled on ice to dissociate non ligated oligonucleotides and ethanol precipitate.

Blocks 1, 2, 3 and 4 were purified as follows. Each ligation mix was run on a 3% low melting agarose gel. No band of the expected size was visible on the gel. However, DNA was extracted from the region of the gel where the gene block was expected to be. The rationale was that there was a small amount of the correct gene block present.

The DNA extracted from the agarose gel was amplified by the polymerase chain reaction (with the NE Biolabs Vent DNA polymerase, 1 cycle 30 sec at 98° C., 25–30 cycles 30 sec at 98° C., 40 sec at 50°~55° C. and 2 min at 72° C., 1 cycle 10 min at 72° C., and cooled at 6° C. The primers were complementary to the ends of the gene blocks and contained a few extra bases so that the entire recognition sites for the specific restriction enzymes flanking each block would be present in each complete block. Blocks were then cloned into the SmaI site of pUC18 or pUC19 plasmids.

Assembled gene blocks were sequenced by the dideoxyterminator method (Sanger, and Coulson, 1975, J. Mol. Biol. 94, 441–448). Typically, 5–12 clones had to be sequenced for each gene block in order to identify one with the expected sequence.

Figure 2A:
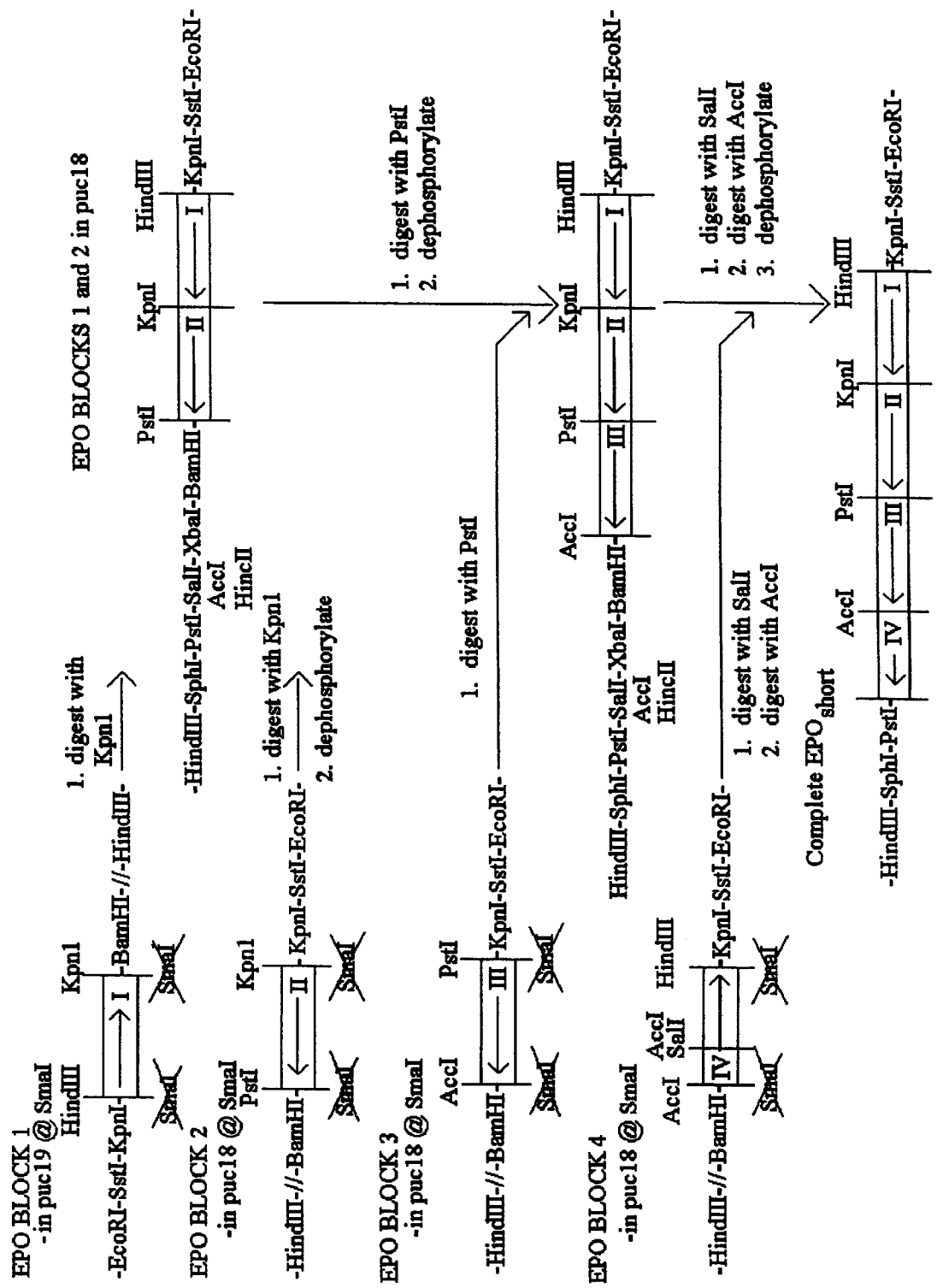
FIG. 2A is a schematic representation of the procedure for synthesizing the EPO$_{short}$ sequence.
Figure 2B:
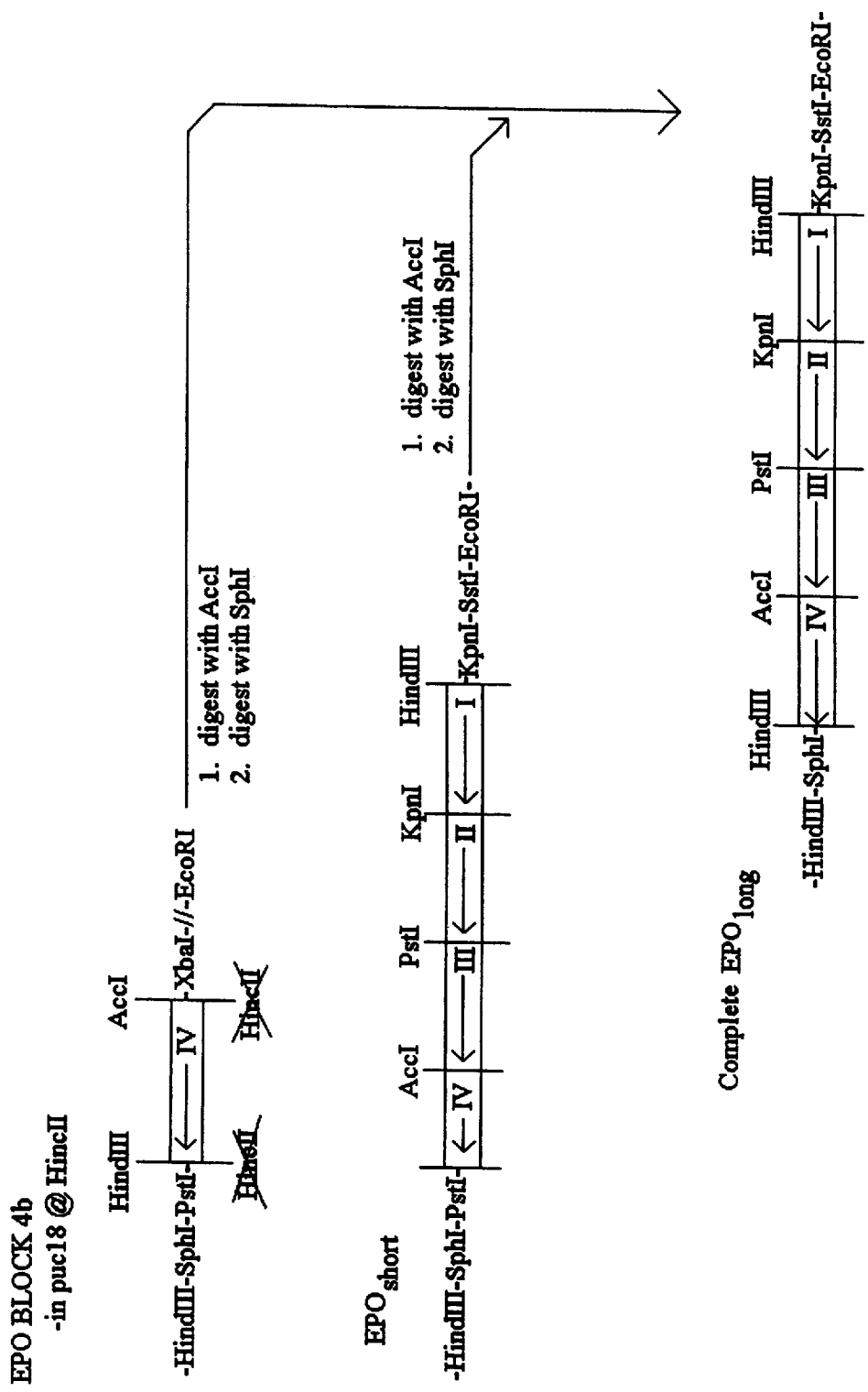
FIG. 2B is a schematic representation of the procedure for synthesizing the EPO$_{Long}$ sequence.

EPO cDNA sequences were assembled as described in Example 2 herein. EPO$_{short}$ and EPO$_{Long}$ cDNA were assembled into pUC18 as shown in FIGS. 2A and 2B, to generate pLW20 and pLW21, respectively.

Example 2

Assembly of Expression Vectors
Synthesis and assembly of EPO cDNA

Two EPO cDNA sequences were chemically synthesized: EPO$_{short}$ and EPO$_{Long}$. The reason for making both a long and a short version of the gene was based on previous results while expressing another gene in COS cells. It had been noted that reducing the length of the 3' non-coding sequence coincided with increased expression of the gene. However, this was not observed with EPO. Therefore the constructs used for this example contained the EPO$_{Long}$ cDNA, as shown in SEQ ID NO. 35 and FIG. 4.

FIG. 1A, provides a schematic representation of the synthesis and assembly of the EPO$_{Long}$ cDNA sequence (SEQ ID NO. 35 and FIG. 4) from the oligonucleotides. Briefly, the coding and complementary strands from contiguous oligonucleotides which had an average length of 60 bases were synthesized. The breakpoints between the oligonucleotides were chosen such that when two complementary oligonucleotides annealed, cohesive ends compatible with those of the adjoining oligonucleotide pair were created. The EPO$_{Long}$ cDNA (SEQ ID NO. 35 and FIG. 4) was constructed from fifteen oligonucleotide pairs, shown in FIG. 1B and SEQ ID NOS. 1–32). The coding strand oligonucleotides were numbered from 1 to 15 except for 13 which was replaced with 13b, and the complementary strand oligonucleotides were numbered 1α to 15α except for 13α which was replaced with 13bα.

The fifteen oligonucleotide pairs were assembled in four blocks. Each junction between adjacent blocks constitutes a unique restriction site. Only three silent mutations were introduced into the EPO$_{Long}$ cDNA sequence for the creation of unique restriction sites: (1) C at position 22 was replaced with A, to add a BstXI site, (2) C at position 256 was replaced with T, to remove a PstI site, and (3) C at position 705 was replaced with T, to add a SspI site. The assembly of the four blocks was done in PUC18, leading to the vector pLW21. pLW21 is the pUC18 vector with the 788 bp EPO$_{Long}$ cDNA sequence, as shown in SEQ ID NO. 35 and FIG. 4, inserted in the HindIII restriction site.

Isolation of genomic EPO DNA

A human leukocyte genomic library was purchased from Clontech and was screened by plaque hybridization with fragments of EPO cDNA as probes. A 2.4 kb (2,365 bp) EPO genomic clone was isolated. This clone spans the HUMERPA sequence (Genbank, accession number M11319) (SEQ ID NO. 33 and FIGS. 3A and 3B) from nucleotide 499 to nucleotide 2365, that is to say its 5' end maps 126 nucleotides upstream of the ATG initiation coding of the EPO pre-protein. The rationale for isolating the EPO gene was that the length of the DNA between the SAR elements would be longer and might allow for an increased effect of the SAR elements.

SAR elements

Two human apolipoprotein B (apoB) SAR elements were used which co-map with the boundaries of the human apolipoprotein B gene chromatin domain (Levy-Wilson & Fortier, 1989, J. Biol. Chem. 264:21196). The following clones were used: Rh10 carrying the distal 1212 bp-long 5'human apoB SAR element and 1317 bp of proximal sequence (SEQ ID NO. 37 and FIG. 6) and a clone (Rh32) carrying the 605 bp long 3'hu apoB SAR element (SEQ ID NO. 36 and FIG. 5).

The DNA sequence of Rh10 was determined by dideoxyterminator method (Sanger, F. and Coulson, A. R., 1975, J. Mol. Biol. 94:441) and is shown in SEQ ID NO. 37 and FIG. 6. The 2529 bp Rh10 sequence consists of the 1212 bp 5' distal human apoB SAR elements and the 1317 bp 5' proximal sequence in the 5' to 3' orientation. The DNA sequence of Rh32 was also determined, and was found to be identical to the sequence published in Levy-Wilson & Fortier (1989, J. Biol. Chem. 264:21196) (SEQ ID NO. 36 and FIG. 5), except for a 60 base pair deletion spanning nucleotides 259 to 318, shown within brackets in FIG. 5. Contrary to Rh10 which is not a typical SAR sequence, Rh32 is A/T rich and contains 22 copies of the ATATTT motif.

Regulatory Elements of Expression Vectors

Figure 7:
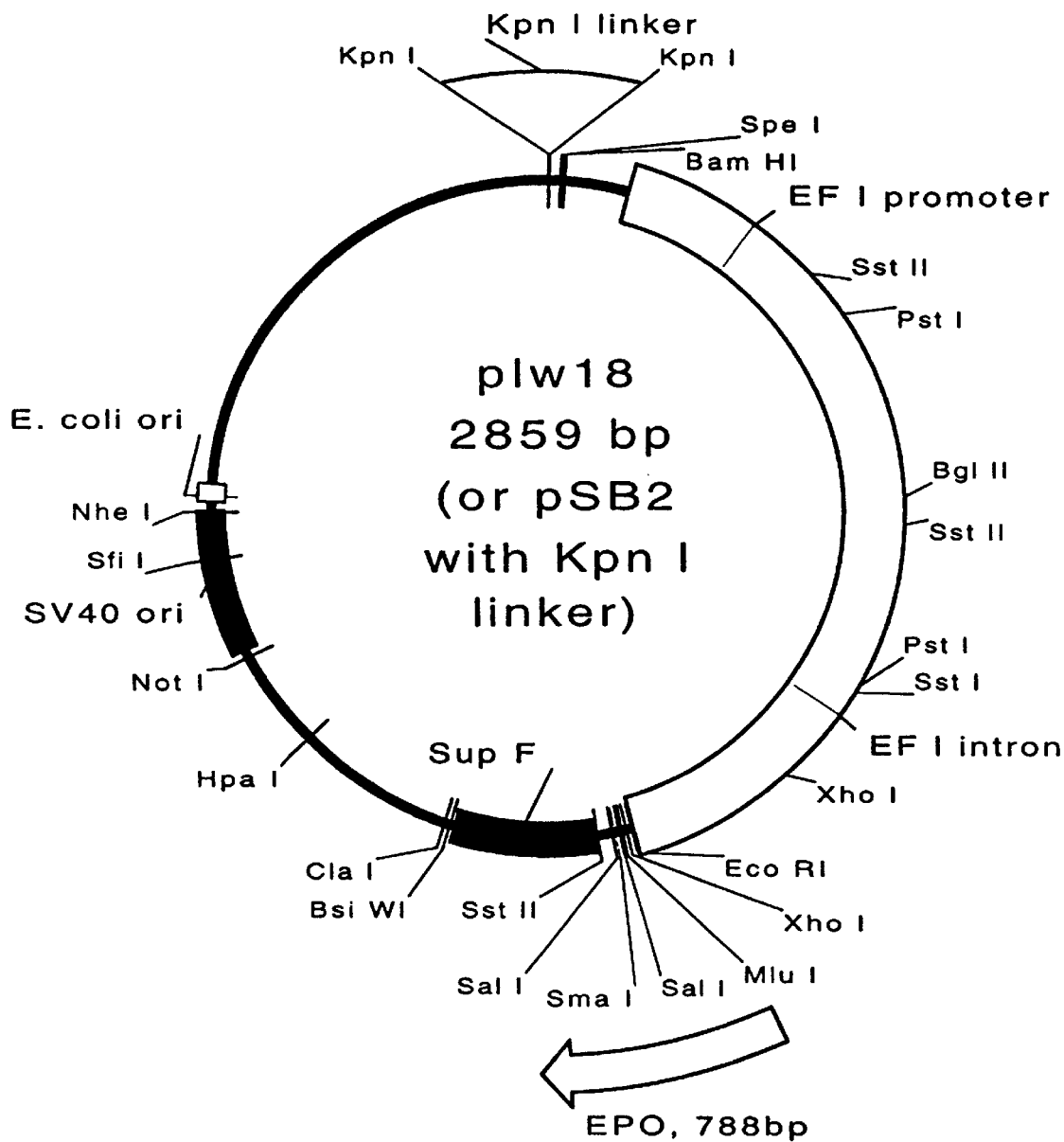
FIG. 7 shows a restriction map of the vector pLW18.
Figure 8:
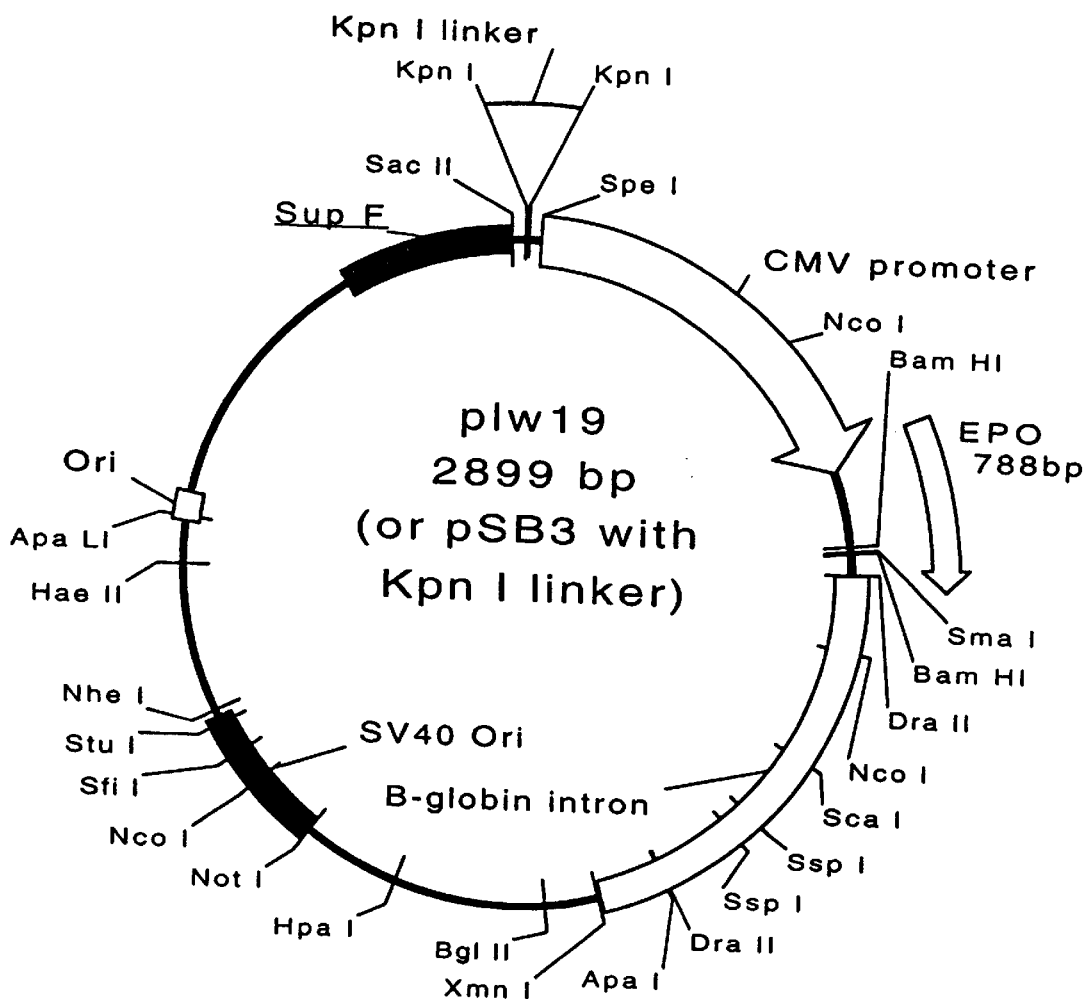
FIG. 8 shows a restriction map of the vector pLW19.

Two basic expression vectors were derived from epAX111 and pAX142 (renamed pLW19 or pSB3 and pLW18 or pSB2, respectively). pAX111 (Kay & Humphries, Methods Mol. Cell. Biol. 2:254, 1991) carries the human cytomegalovirus IE enhancer and promoter and the β-globin intron, while pAX142 carries the elongation factor-1α promoter and intron. For each of these vectors there are single restriction sites located on each site of the EPO transcription unit, where the SAR elements were introduced (SpeI or EcoRV at the 5'end and HpaI at the 3'end). Maps of the two vectors pLW18 (pSB2) and pLW19 (psB3) are shown in FIGS. 7 and 8 respectively.

Assembly of Expression Vectors

The $EPO_{Long}$ cDNA sequence (SEQ ID NO.35, FIG. 4) or the genomic EPO DNA (SEQ ID NO. 33, FIGS. 3A and 3B) were introduced clockwise into the cloning sites of the expression vectors. In the case of the genomic clones, the β-globin and EF1 introns were removed from the pSB3 and pSB2 vectors, respectively. A summary of the expression vectors is shown in Table 1.

Construction of pLW24 and pLW25 Vectors

The $EPO_{Long}$ cDNA (SEQ ID NO.35, FIG. 4) was removed from pLW21 by digestion with HindIII, was blunt-ended with the T4 DNA polymerase and was introduced in the clockwise orientation into the SmaI site of pLW18 and pLW19 to generate pLW24 and pLW25, respectively.

Construction of p24MAR1 and p25MAR1

Introduction of the 5' human apoB SAR element at the 5' end of the EPO transcription unit was accomplished as follows. The 2,529 bp XbaI fragment from Rh10 (SEQ ID NO. 37, FIG. 6) was introduced in the clockwise orientation into the SpeI site of pLW24 and pLW25 to generate p5MAR24 and p5MAR25, respectively (Note that XbaI and SpeI sites are compatible).

Introduction of the 60 bp-deleted 3' human apoB SAR element at the 3' end of the EPO transcription unit was accomplished as follows. The 605 bp DraI-RsaI fragment from the plasmid 12 DI Eco was added XhoI linkers and cloned into the XhoI site of the Stratagene pSBII SK(+) plasmid, to generate plasmid 3'apoBX (Rh32) (SEQ ID NO. 36, FIG. 5). The ~605 bp SAR fragment was then removed from Rh32 by XhoI digestion, blunt-ended with the Klenow enzyme and cloned into the HpaI site of p5MAR24 and p5MAR25 to generate p24MAR-1 and p25MAR-1, respectively. The orientation of the inserted fragments has not yet been determined.

Construction of pAP142 and DAP140

Plasmids pSB2 and pSB3 were derived from pLW18 and pLW19, respectively. A 12 bp DNA linker with the EcoRV and SphI restriction sites was inserted into the KpnI site of pLW18 and pLW19 to generate pSB2 and pSB3, respectively. This allowed for introduction of SAR elements into the blunt-end EcoRV restriction site, just upstream of the EPO transcription unit.

The $EPO_{Long}$ cDNA sequence was removed from pLW24 by digestion with SalI and cloned in the clockwise orientation into the SalI site of pSB2 to generate pAP13. pAP5 was generated by removing the $EPO_{Long}$ cDNA sequence from pLW25 by digestion with BamHI and cloning in the clockwise orientation into the BamHI site of pSB3 to generate pAP5.

The Rh32 $^{-605}$ bp XhoI SAR fragment (60 bp-deleted 3' human apoB SAR element) was blunt-ended with the T4 DNA polymerase and inserted in the clockwise orientation into the EcoRV site of PAP13 and pAP5 to generate pAP138 and pAP136, respectively. The same Rh32 $^{-605}$ bp XhoI blunt-ended SAR fragment was inserted in the clockwise orientation into the HpaI site of pAP138 and pAP136 to generate pAP142 and pAP140, respectively.

Construction of pAP59 and pAP67 pAP42 is an intronless version of pSB2. pSB2 was amplified by the polymerase chain reaction between nucleotides 1308 and 321, and the amplified fragment was ligated on itself to produce pAP42. pAP43 is an intronless version of pSB3. The SmaI-XmnI fragment (nucleotides 677 –1320) was removed from pSB3 to produce pAP43.

The EPO genomic clone was isolated from a Clontech library (Cat. No. HL1006d; Lot No. 19412) by probing with the BamHI $EPO_{short}$ cDNA fragment from pAP4. The $EPO_{short}$ cDNA fragment used as a probe to isolate the genomic EPO clone was a BamHI fragment from pAP4. As for $EPO_{Long}$ cDNA, $EPO_{short}$ cDNA was first assembled into the HindIII site of the pUC18 vector, to generate the pLW20 vector, blunt-ended with the T4 DNA polymerase and inserted in the clockwise orientation into the SmaI site of pLW19 to generate pLW23. Then the $EPO_{short}$ cDNA sequence was removed from pLW23 by BamHI digestion and cloned in the clockwise orientation into the BamHI site of pSB3 to generate pAP4.

Plaque hybridization was performed according to the method described in "Molecular Cloning. A Laboratory Manual, 2nd Edition. 1989". Edited by Sambrook, Fritsch, and Maniatis, Cold Spring Harbor Laboratory Press. pp 2.108–2.121. A 7.5 kb BamHI fragment (cloned in the Stratagene pBS (KS+) plasmid) was identified as an EPO genomic clone. The identity of this clone was confirmed by polymerase chain reaction between primers EPOGEN 1 (nucleotides 499–518 in HUMERPA sequence) and EPO-GEN 12 (nucleotides 2848–2863, on complementary strand, in HUMERPA sequence). This resulted in the expected fragment. The 2,365 bp amplified fragment was cloned in the clockwise orientation into the HincII site of pUC19 to generate pAP41. The EPO genomic sequence was then removed from pAP41 by EcoRI and HindIII digestion, blunt-ended with the T4 DNA polymerase and inserted in the clockwise orientation into the SmaI site of pAP42 to generate pAP59 or into the blunt-ended BamHI site of pAP43 to generate pAP67.

Construction of pAP123, pAP127, pAP132 and pAP134

The Rh32 $^{-605}$ bp XhoI SAR fragment (60 bp-deleted 3' human apoB SAR element) was blunt-ended with the T4 DNA polymerase and inserted in the clockwise orientation into the HpaI site of pAP59 and pAP67 to generate pAP117 and pAP119, respectively. The same Rh32 ~605 bp XhoI blunt-ended SAR fragment was inserted in the clockwise orientation into the EcoRV site of pAP117 and pAP119 to generate pAP123 and pAP127, respectively.

The 2,529 bp XbaI fragment from Rh10 was blunt-ended with the T4 DNA polymerase, and introduced in the clockwise orientation into the EcoRV site of pAP117 and pAP119 to generate pAP132 and pAP134, respectively.

Example 3

Transfection and Expression of EPO

Transfection

Briefly as described in more detail below CHO-K1 cells were co-transfected by the calcium phosphate precipitate method by two pairs of vectors: pSV2-neo carrying the resistance to the selective agent G-418 and one of the two following vectors expressing the EPO cDNA from the EF1 promoter: pLW24 or p24-MAR. pLW24 had no SAR element, while p24-MAR had the 5'apo B SAR element (Rh10) upstream of the EF 1 promoter region and the 60 bp-deleted 3'apoB SAR element (Rh32) downstream of the EPO cDNA.

G-418 was added to the medium to select cells transfected with pSV2-neo. At least 80% of these transfectants were expected to have been co-transfected with the EPO vector.

The following protocol was used for transfection with the Mammalian Transfection Kit by Stratagene (Catalog #200285). On day-1 100 mm culture dishes were inoculated with exponentially growing mammalian cells at a concentration of $5 \times 10^4$ cells per ml in 10 ml. The cells were grown overnight at 37° C. with the appropriate level of $CO_2$ and in appropriate medium. For CHO-K1 cells Ham's F12 complete medium with 10% fetal calf serum (FCS) was used and incubation was carried out with 5% $CO_2$. The cells were approximately 10–20% confluent on day zero.

The optimal amount of DNA to be used for transfection varied depending on the cell type being used for transfection. Usually, 10–30 µg of plasmid DNA was used. The plasmid used for selection was generally added at some ratio to the expression vector. For pSV2neo, a ratio of 1:10 to 1:15 was found to be appropriate.

The desired amount of DNA was diluted to 450 µl with double distilled $H_2O$. 50 µl of solution 1 (2.5M Ca $Cl_2$, included in the Stratagene kit) was added slowly and dropwise. 500 µl of Solution 2 (2×BBS, pH 6.95 [consists of 50 mM n, n-bis (2-hydroxyethyl)-2-aminoethanesulfonic acid and buffered saline, 280 mM NaCl and 1.5 mM $Na_2$ $HPO_4$]) was added and mixed gently and slowly. It was found to be important to perform these two additions slowly and gently. The mixture was allowed to incubate at room temperature for 10–20 minutes. The precipitate was gently mixed to ensure adequate suspension. The precipitate was added to the culture dropwise while gently swirling the plate to distribute the suspension evenly, followed by incubation for 12–24 hours.

Where spare incubator space was available, it was determined that transfection efficiency could be improved 2–3 times by using lower $CO_2$ concentrations at this point (2–4% is recommended; 3% seemed to work well with CHO cells). Normal $CO_2$ concentrations were resumed after removal of precipitate on Day 1.

On day 1 the medium was removed by aspiration and the culture rinsed twice with sterile PBS (Phosphate buffered saline without $Ca^{2+}$, $Mg^{2+}$) or medium without serum. Fresh complete medium was applied (as on Day-1) and the cells incubated under optimal $CO_2$ concentration for 24 hours.

The cells were split at a ratio ranging from 1:30 to 1:100 into 96 well plates (0.2 ml per well). For CHO-K1 cells, Ham's F12 complete medium with 20% FCS was used at this step. Incubation was carried out at 37° C. with 5% $CO_2$.

On day 4 the medium was aspirated and selective medium was added. For transfections using CHO-K1cells and pSV2neo as the selective plasmid, Ham's F12 complete medium with 20% FCS+270–400 µg/ml G418 was used.

On day 5 or 6 (preferably day 5) and on day 8, the cultures were refed with selective medium.

On day 10, spent medium was collected for RIA assays and frozen. The spent medium was replaced with selective medium.

From day 11 RIA assays, were performed to determine levels of EPO production in the medium, using undiluted samples. Samples producing high levels of EPO were cloned and subcultured in Ham's F12 complete medium with 10% FCS when they reached confluency.

EPO Production

Levels of EPO production in the medium were determined by RIA as follows.

The following materials and equipment were used in the assay: phosphate RIA buffer: 0.05M $NaPO_4$; 0.2% BSA; 0.02% $NaN_3$, pH 7.4; Erythropoietin (standards, Boehringer Mannheim, Cat. #1120166, 250 u/ml); $^{125}$I-EPO (Amersham Cat. #IM.219); anti-rabbit IgG (whole molecule) developed in goat, whole antiserum (Sigma Cat. #R-5001 (abbrev. Ab2) polyethylene glycol 8000 (BDH Cat. #B80016); normal rabbit serum (abbrev. NRS); Rabbit anti-EPO, polyclonal, 1 mg (abbrev. Ab1) (R&D Systems Cat. #AB-286-NA) and; gamma counter (LKB-Wallac RIAGamma 1272).

The stock concentration of EPO was 250 U/ml. Eight standard concentrations were prepared from a stock dilution of 20 U/ml sufficient for 4.5 ml of each standard or 20 assays in duplicate. 20 U/ml=88 µl @ 250 U/ml +1012 µl dilution buffer. The eight standard concentrations are shown in Table 2. The standards were divided into 450 µl aliquots in microcentrifuge tubes and stored at −20° C. until used.

Antibody 1 (1 mg) was dissolved in 1 ml RIA/DB and stored in 20 µl aliquots in 0.5 ml microcentrifuge tubes at −20° C. until used (each aliquot was sufficient for 100 assay tubes). On the assay date, Ab1 was prepared at a working concentration of 2 µg/ml with dilution buffer (a 1/500 dilution of the stock aliquot) to give a final assay concentration of 0.67 µg/ml in 300 µl when added as 100 µl to all tubes except non-specific binding (NSB) and total counts (TC).

Since all standard and sample binding inhibition % were based on the maximum binding (MB), to avoid the possibility of having a poor reference duplicate, the MB was determined in quadruplicate.

The $^{125}$I-EPO was diluted with 4.5 ml of dilution buffer and divided into 25×0.2 ml aliquots in 500 µl microcentrifuge tubes. A 5 µl sample was added to 50 µl of dilution buffer in an 11×75 mm tube and counted for 1 min. in the RIAGamma using program 2. The corrected CPM usually ranged between 4500–6000 CPM/µl. The tracer aliquots were stored, with lead shielding, at −20° C. until used.

Table 3 lists the assay setup and addition of reagents. The reagents were added and incubated in the following order: A) dilution buffer and NRS @ 1/33.3 were added to the appropriate tubes 3–8; B) EPO standards and sample dilutions were added to the appropriate tubes; C) antibody 1 was added to all tubes except 1–4 and; all tubes were vortexed and incubated at room temperature for 4h. $^{125}$I-EPO @ 6000 CPM/100 µl was added to all tubes. As the tracer activity decreases over time, the maximum binding % decreases resulting in a loss of sensitivity and accuracy. Therefore, we used 6000 CPM total counts during the first week of a new batch and increased by 1000 CPM per week thereafter.

All tubes (except TC's) were vortexed and incubated overnight (18–20 hours) @ 40° C. Ab 2 and NRS (1/62.5) was added to all tubes except TC's. All tubes (except TC's) were vortexed and incubated at room temperature for 2 hours. 1.5 ml of 3.8% PEG 8000 (w/v in dilution buffer) was added to all tubes (except TC's) resulting in a final PEG concentration of 3%. All tubes (except TC's) were vortexed and incubated for 10 minutes at room temperature. All tubes were centrifuged (except TC's) at 1500×g and 4° C. for 20 minutes (1500×g=2800 RPM when using the IEC Centra-8R with the Cat. #5737 12×75 mm tube adapters). The supernants were removed by aspiration and the tubes containing the pellets were counted in the gamma counter.

The standard curve was plotted using linear regression of logit (B/Bo) vs log concentration where B=CPM bound and, Bo=maximum CPM bound (reference binding of Ab 1 without inhibitor). The regression line y=C0+C1(x) where, C0=y intercept, C1=slope, x=Log (Concentration), y=Log (R/(1-R)) and, R=B/Bo.

Interference of culture medium was tested by the addition of up to 95 $\mu$l of a possible 100 $\mu$l sample volume of Ham's F-12 containing 10% FCS. No effect on binding was observed. Recovery of EPO at 100, 300, and 600 mU/ml was 93.85, 100.41, and 96.33% respectively.

Screening was performed as follows. The assay was performed in one day for screening samples by using the following modifications to the above-noted method. Standards and sample dilutions were incubated with Ab1 for 1 hour at 37° C. instead of 4 hours at room temperature. $^{125}$I-EPO was incubated with all tubes for 1 hour at 37° C. instead of overnight at 4° C. Antibody 2 and NRS are incubated for 1 hour at 37° C. instead of 2 hours at room temperature. The remaining procedures were as described above and the results are given below.

The first transfection series was performed with the following target vectors: PLW24 (EF1 promoter, $EPO_{Long}$) referred to as EPO-1 or; p24MAR-1 (EF1 promoter, $EPO_{Long}$, 5'apoB & 3' 60 bp-deleted apoB SAR elements) referred to as EPO-1*. The selection plasmid was pSV2neo. The target:selection plasmid ratio was 5:1 (30 $\mu$g:6 $\mu$g).

One sample was picked up randomly from each transfection and was cloned by the dilution method. EPO-1-0-1 was cloned from the EPO-1 transfection and EPO-1-0-4* from the EPO-1* transfection (* indicates the presence of SAR elements in the target vector).

After the first round of cloning, the two EPO-1 clones and four EPO-1* clones expressing the highest levels of EPO were selected and expanded. Levels of EPO production in the medium, determined by the RIA assays were as follows: EPO-1-1-5: 8 u/10$^6$ cells/day; EPO-1-1-6:9 u/10$^6$ cells/day; EPO-1-1-7*: 41 u/10$^6$ cells/day; EPO-1-1-8*: 30 u/10$^6$ cells/day; EPO-1-1-13*: 125 u/10$^6$ cells/day and; EPO-1-1-14*: 81 u/10$^6$ cells/day.

After a second round of cloning, levels of EPO expression were as follows: EPO-1-2-22: 5 u/10$^6$ cells/day; EPO-1-2-23: 7 u/10$^6$ cells/day; EPO-1-2-26: 13 u/10$^6$ cells/day; EPO-1-2-27: 19 u/10$^6$ cells/day; EPO-1-2-15*: 13 u/10$^6$ cells/day; EPO-1-2-16*: 20 u/10$^6$ cells/day and; EPO-1-2-17*: 105 u/10$^6$ cells/day.

The second transfection series was performed with the same target and selection vectors as the first transfection series. The target plasmid:selection plasmid ratio was 12:1 (30 $\mu$g:2.5 $\mu$g).

At day 10 after transfection, EPO-2-0-11 (producing 0.8 u/ml EPO) from EPO-2 transfection (target plasmid has no SAR elements) and EPO2-0-9* (producing 0.6 u/ml) from EPO-2* transfection (target plasmid with SAR elements) were selected for cloning. 21 days after cloning, the levels of EPO production in the medium for EPO-2-0-11 were as follows: 36/48 samples had <160 u/ml; 11/48 samples had 160–800 u/ml; and 1/48 samples had 800 u/ml. Levels of EPO production for EPO-2-0-9* were as follows: 47/48 samples had 1,000–4,000 u/ml and; 1/48 samples had <800 u/ml.

Two of the EPO-2 clones and three of the EPO-2* clones (expressing the highest levels of EPO per cell cluster) were expanded, and the levels of expression were as follows: EPO-2-1-24 (514 u/ml 21 days after cloning) and 109 u/10$^6$ cells/day after expansion; EPO2-1-25 (800 u/ml 21 days after cloning) and 182 u/10$^6$ cells/day after expansion; EPO-2-1-18* (1,962 u/ml 21 days after cloning) and 185 u/10$^6$ cells/day after expansion; EPO-2-1-19* (1,682 u/ml 21 days after cloning) and 1,306 u/10$^6$ cells/day after expansion and; EPO-2-1-21* (1,777 u/ml 21 days after cloning) and 332 u/10$^6$ cells/day after expansion.

EPO-2-1-19* was found to maintain its levels of EPO production while submitted to successive freezing-revival cycles as follows: 962 and 1,038 u/10$^6$ cells/day after the first cycle; 1,323 and 1,264 u/10$^6$ cells/day (between days 3 and 4) after the second cycle and; 1,188 u/10$^6$ cells/day (between days 3 and 4) after the third cycle.

EPO-2-1-19* was submitted to a second round of cloning. The clones producing the highest levels of EPO produced between 1,500 and 1,700 u/10$^6$ cells/day (between days 3 and 4). The EPO-2-1-19* cell line has remained stable and expressed constant levels of EPO for about eight months.

TABLE 1

| Assembly of expression vectors | | | | |
|---|---|---|---|---|
| EF1 promoter | CMV promoter | EPO sequence | 5' SAR element | 3' SAR element |
| pLW24 Rh49 | pLW25 Rh216 | $cDNA_{long}$ | — | — |
| p24MAR-1 Rh163 | p25MAR-1 Rh101 | $cDNA_{long}$ | Rh10 | Rh32 |
| pAP142 Rh223 | pAP140 Rh233 | $cDNA_{long}$ | Rh32 | Rh32 |
| pAP59 Rh183 | pAP67 Rh209 | genomic | — | — |
| pAP123 Rh211 | pAP127 Rh201 | genomic | Rh32 | Rh32 |
| pAP132 Rh221 | pAP134 Rh222 | genomic | Rh10 | Rh32 |

TABLE 2

| Standard No. | 20 U/ml Stock ($\mu$l) | Dilution Buffer ($\mu$l) | Standard Concentration (mU/ml) |
|---|---|---|---|
| 1 | 4.5 | 4495.5 | 20 |
| 2 | 9.0 | 4491.0 | 40 |
| 3 | 18.0 | 4482.0 | 80 |
| 4 | 36.0 | 4464.0 | 160 |
| 5 | 67.5 | 4432.5 | 300 |
| 6 | 135.0 | 4365.0 | 600 |
| 7 | 270.0 | 4230.0 | 1,200 |
| 8 | 450.0 | 4050.0 | 2,000 |

TABLE 3

| Tube # | Code | Dilution Buffer (μl) | NRS @ 1/33.3 (μl) | EPO Standard (μl) | Ab1 @ 2 μg/ml (μl) | I-EPO 6000 CPM (μl) | Ab2 @ 1/5 (μl) | NRS @ 1/62.5 (μl) |
|---|---|---|---|---|---|---|---|---|
| 1–2 | TC | 0 | 0 | 0 | 0 | 100 | 0 | 0 |
| 34 | NSB | 100 | 100 | 0 | 0 | 100 | 50 | 50 |
| 5–8 | MB | 100 | 0 | 0 | 100 | 100 | 50 | 50 |
| Standard Curve | | | | | | | | |
| 9–10 | 20 mU/ml | 0 | 0 | 100 | 100 | 100 | 50 | 50 |
| 11–12 | 40 mU/ml | 0 | 0 | 100 | 100 | 100 | 50 | 50 |
| 13–14 | 80 mU/ml | 0 | 0 | 100 | 100 | 100 | 50 | 50 |
| 15–16 | 160 mU/ml | 0 | 0 | 100 | 100 | 100 | 50 | 50 |
| 17–18 | 300 mU/ml | 0 | 0 | 100 | 100 | 100 | 50 | 50 |
| 19–20 | 600 mU/ml | 0 | 0 | 100 | 100 | 100 | 50 | 50 |
| 21–22 | 1200 mU/ml | 0 | 0 | 100 | 100 | 100 | 50 | 50 |
| 23–24 | 2000 mU/ml | 0 | 0 | 100 | 100 | 100 | 50 | 50 |
| Inter/Intra-assay Quality Controls | | | | | | | | |
| 25–26 | 100 mU/ml | 0 | 0 | 100 | 100 | 100 | 50 | 50 |
| 27–28 | 400 mU/ml | 0 | 0 | 100 | 100 | 100 | 50 | 50 |
| 29–30 | 800 mU/ml | 0 | 0 | 100 | 100 | 100 | 50 | 50 |
| Unknowns | | | | | | | | |
| 31–32 | Sample 1 | 100 μl of Sample Dilution | 0 | 0 | 100 | 100 | 50 | 50 |

---

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO1

( x i ) SEQUENCE DESCRIPTION: SEQ ID NO:1:

AGCTTGCCCG GGATGAGGGC CACCGGTGTG GTCACCCGGC GCGCCCAGG T    51

( 2 ) INFORMATION FOR SEQ ID NO:2:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO2

( x i ) SEQUENCE DESCRIPTION: SEQ ID NO:2:

CGCTGAGGGA CCCCGGCCAG GCGCGGAGAT GGGGGTGCAC GAAT    44

( 2 ) INFORMATION FOR SEQ ID NO:3:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO3

( x i ) SEQUENCE DESCRIPTION: SEQ ID NO:3:

GTCCTGCCTG GCTGTGGCTT CTCCTGTCCC TGCTGTCGCT CCCTCTGGGC C    51

( 2 ) INFORMATION FOR SEQ ID NO:4:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO4

( x i ) SEQUENCE DESCRIPTION: SEQ ID NO:4:

TCCCAGTCCT GGGCGCCCCA CCACGCCTCA TCTGTGACAG CCGAGTCCTG GAGAGGTAC    59

( 2 ) INFORMATION FOR SEQ ID NO:5:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO5

( x i ) SEQUENCE DESCRIPTION: SEQ ID NO:5:

CTCTTGGAGG CCAAGGAGGC CGAGAATATC ACGACGGCT GTGCTGAACA TTGCAG    56

( 2 ) INFORMATION FOR SEQ ID NO:6:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
            ( B ) CLONE: EPO6

( x i ) SEQUENCE DESCRIPTION: SEQ ID NO:6:

CTTGAATGAG AATATCACTG TCCCAGACAC CAAAGTTAAT TTCTATGCCT GGAAGAGG          58

( 2 ) INFORMATION FOR SEQ ID NO:7:

( i ) SEQUENCE CHARACTERISTICS:
            ( A ) LENGTH: 55 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( v i i ) IMMEDIATE SOURCE:
            ( B ) CLONE: EPO7

( x i ) SEQUENCE DESCRIPTION: SEQ ID NO:7:

ATGGAGGTCG GGCAGCAGGC CGTAGAAGTC TGGCAGGGCC TGGCCCTGCT GTCGG            55

( 2 ) INFORMATION FOR SEQ ID NO:8:

( i ) SEQUENCE CHARACTERISTICS:
            ( A ) LENGTH: 61 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( v i i ) IMMEDIATE SOURCE:
            ( B ) CLONE: EPO8

( x i ) SEQUENCE DESCRIPTION: SEQ ID NO:8:

AAGCTGTCCT GCGGGGCCAG GCCCTGTTGG TCAACTCTTC CCAGCCGTGG GAGCCCCTGC       60
A                                                                      61

( 2 ) INFORMATION FOR SEQ ID NO:9:

( i ) SEQUENCE CHARACTERISTICS:
            ( A ) LENGTH: 54 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( v i i ) IMMEDIATE SOURCE:
            ( B ) CLONE: EPO9

( x i ) SEQUENCE DESCRIPTION: SEQ ID NO:9:

GCTGCATGTG GATAAAGCCG TCAGTGGCCT TCGCAGCCTC ACCACTCTGC TTCG             54

( 2 ) INFORMATION FOR SEQ ID NO:10:

( i ) SEQUENCE CHARACTERISTICS:
            ( A ) LENGTH: 51 base pairs
            ( B ) TYPE: nucleic acid
            ( C ) STRANDEDNESS: single (D) TOPOLOGY: linear (ii) MOLECULE TYPE: cDNA (vi) ORIGINAL SOURCE:
    (A) ORGANISM: Homo sapiens (vii) IMMEDIATE SOURCE:
    (B) CLONE: EPO10

(xi) SEQUENCE DESCRIPTION: SEQ ID NO:10:

GGCTCTGGGA GCCCAGAAGG AAGCCATCTC CCCTCCAGAT GCGGCCTCAG C    51

(2) INFORMATION FOR SEQ ID NO:11:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (vii) IMMEDIATE SOURCE:
        (B) CLONE: EPO11

(xi) SEQUENCE DESCRIPTION: SEQ ID NO:11:

TGCTCCACTC CGAACAATCA CTGCTGACAC TTTCCGCAAA CTCTTCCGAG T    51

(2) INFORMATION FOR SEQ ID NO:12:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (vii) IMMEDIATE SOURCE:
        (B) CLONE: EPO12

(xi) SEQUENCE DESCRIPTION: SEQ ID NO:12:

CTACTCCAAT TTCCTCCGGG GAAAGCTGAA GCTGTACACA GGGGAGG    47

(2) INFORMATION FOR SEQ ID NO:13:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (vii) IMMEDIATE SOURCE:
        (B) CLONE: EPO13

(xi) SEQUENCE DESCRIPTION: SEQ ID NO:13:

CCTGCAGGAC AGGGGACAGA TGACCAGGTG TGTCGACCTG GGCATATC    48

(2) INFORMATION FOR SEQ ID NO:14:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( v i i ) IMMEDIATE SOURCE:
    ( B ) CLONE: EPO13b ( x i ) SEQUENCE DESCRIPTION: SEQ ID NO:14:

CCTGCAGGAC AGGGGACAGA TGACCAGGTG TGTCCACCTG GGCATATC          48

( 2 ) INFORMATION FOR SEQ ID NO:15:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO15

( x i ) SEQUENCE DESCRIPTION: SEQ ID NO:15:

CACCACCTCC CTCACCAATA TTGCTTGTGC CACACCCTCC CCCGCCACTC          50

( 2 ) INFORMATION FOR SEQ ID NO:16:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO15

( x i ) SEQUENCE DESCRIPTION: SEQ ID NO:16:

CTGAACCCCG TCGAGGGGCT CTCAGCTCAG CGCCAGCCTG TCCCATGGAC CA          52

( 2 ) INFORMATION FOR SEQ ID NO:17:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO1 alpha ( x i ) SEQUENCE DESCRIPTION: SEQ ID NO:17:

CCTCAGCGAC CTGGGGCGCG CCGGGTGACC ACACCGGTGG CCCTCATCCC GGGCA          55

( 2 ) INFORMATION FOR SEQ ID NO:18:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO2 alpha ( x i ) SEQUENCE DESCRIPTION: SEQ ID NO:18:

GGCAGGACAT TCGTGCACCC CCATCTCCGC GCCTGGCCGG GGTC    44

( 2 ) INFORMATION FOR SEQ ID NO:19:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO3 alpha ( x i ) SEQUENCE DESCRIPTION: SEQ ID NO:19:

GGACTGGGAG GCCCAGAGGG AGCGACAGCA GGGACAGGAG AAGCCACAGC CA    52

( 2 ) INFORMATION FOR SEQ ID NO:20:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO4 alpha ( x i ) SEQUENCE DESCRIPTION: SEQ ID NO:20:

CTCTCCAGGA CTCGGCTGTC ACAGATGAGG CGTGGTGGGG CGCCCA    46

( 2 ) INFORMATION FOR SEQ ID NO:21:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO5 alpha ( x i ) SEQUENCE DESCRIPTION: SEQ ID NO:21:

TTCAGCACAG CCCGTCGTGA TATTCTCGGC CTCCTTGGCC TCCAAGAGGT AC   52

( 2 ) INFORMATION FOR SEQ ID NO:22:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO6A ( x i ) SEQUENCE DESCRIPTION: SEQ ID NO:22:

AGGCATAGAA ATTAACTTTG GTGTCTGGGA CAGTGATATT CTCATTCAAG CTGCAATG   58

( 2 ) INFORMATION FOR SEQ ID NO:23:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO7 alpha ( x i ) SEQUENCE DESCRIPTION: SEQ ID NO:23:

AGGGCCAGGC CCTGCCAGAC TTCTACGGCC TGCTGCCCGA CCTCCATCCT CTTCC   55

( 2 ) INFORMATION FOR SEQ ID NO:24:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: EPO8 alpha ( x i ) SEQUENCE DESCRIPTION: SEQ ID NO:24:

GGGGCTCCCA CGGCTGGGAA GAGTTGACCA ACAGGGCCTG GCCCCGCAGG ACAGCTTCCG   60

ACAGC   65

( 2 ) INFORMATION FOR SEQ ID NO:25:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
  ( A ) ORGANISM: Homo sapiens ( v i i ) IMMEDIATE SOURCE:
  ( B ) CLONE: EPO9 alpha ( x i ) SEQUENCE DESCRIPTION: SEQ ID NO:25:

AGTGGTGAGG CTGCGAAGGC CACTGACGGC TTTATCCACA TGCAGCTGCA  50

( 2 ) INFORMATION FOR SEQ ID NO:26:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( v i i ) IMMEDIATE SOURCE:
    ( B ) CLONE: EPO10 alpha ( x i ) SEQUENCE DESCRIPTION: SEQ ID NO:26:

CGCATCTGGA GGGGAGATGG CTTCCTTCTG GGCTCCCAGA GCCCGAAGCA G  51

( 2 ) INFORMATION FOR SEQ ID NO:27:

( i ) SEQUENCE CHARACTERISTICS:
    ( A ) LENGTH: 61 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( v i i ) IMMEDIATE SOURCE:
    ( B ) CLONE: EPO11 alpha ( x i ) SEQUENCE DESCRIPTION: SEQ ID NO:27:

AGACTCGGAA GAGTTTGCGG AAAGTGTCAG CAGTGATTGT TCGGAGTGGA GCAGCTGAGG  60
C  61

( 2 ) INFORMATION FOR SEQ ID NO:28:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( v i i ) IMMEDIATE SOURCE:
    ( B ) CLONE: EPO 12 alpha ( x i ) SEQUENCE DESCRIPTION: SEQ ID NO:28:

CCTGCAGGCC TCCCCTGTGT ACAGCTTCAG CTTTCCCCGG AGGAAATTGG AGT  53

( 2 ) INFORMATION FOR SEQ ID NO:29:

( i ) SEQUENCE CHARACTERISTICS:

( A ) LENGTH: 47 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens ( v i i ) IMMEDIATE SOURCE:
( B ) CLONE: EPO13 alpha ( x i ) SEQUENCE DESCRIPTION: SEQ ID NO:29:

GGTGGTGGAT ATGCCCAGGT CGACACACCT GGTCATCTGT CCCCTGT    47

( 2 ) INFORMATION FOR SEQ ID NO:30:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens ( v i i ) IMMEDIATE SOURCE:
( B ) CLONE: EPO13b alpha ( x i ) SEQUENCE DESCRIPTION: SEQ ID NO:30:

GGTGGTGGAT ATGCCCAGGT GGACACACCT GGTCATCTGT CCCCTGT    47

( 2 ) INFORMATION FOR SEQ ID NO:31:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens ( v i i ) IMMEDIATE SOURCE:
( B ) CLONE: EPO14 alpha ( x i ) SEQUENCE DESCRIPTION: SEQ ID NO:31:

GGGTTCAGGA GTGGCGGGGG AGGGTGTGGC ACAAGCAATA TTGGTGAGGG A    51

( 2 ) INFORMATION FOR SEQ ID NO:32:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens ( v i i ) IMMEDIATE SOURCE:
( B ) CLONE: EPO15 alpha ( x i ) SEQUENCE DESCRIPTION: SEQ ID NO:32:

AGCTTGGTCC ATGGGACAGG CTGGCGCTGA GCTGAGAGCC CCTCGACG    48

( 2 ) INFORMATION FOR SEQ ID NO:33:

( i ) SEQUENCE CHARACTERISTICS:
    ( A ) LENGTH: 3602 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Homo sapiens ( i x ) FEATURE:
    ( A ) NAME/KEY: CDS
    ( B ) LOCATION: join(625..637, 1201..1346, 1605..1691, 2303..
        2482, 2617..2772)

( i x ) FEATURE:
    ( A ) NAME/KEY: mRNA
    ( B ) LOCATION: join(625..637, 1201..1346, 1605..1691, 2303..
        2482, 2617..2772)

( i x ) FEATURE:
    ( A ) NAME/KEY: mat_peptide
    ( B ) LOCATION: join(1269..1346, 1605..1691, 2303..2482, 2617
        . . 2769)

( i x ) FEATURE:
    ( A ) NAME/KEY: prim_transcript
    ( B ) LOCATION: join(625..3337)

( x i ) SEQUENCE DESCRIPTION: SEQ ID NO:33:

```
AAGCTTCTGG  GCTTCCAGAC  CCAGCTACTT  TGCGGAACTC  AGCAACCCAG  GCATCTCTGA         60

GTCTCCGCCC  AAGACCGGGA  TGCCCCCCAG  GGGAGGTGTC  CGGGAGCCCA  GCCTTTCCCA        120

GATAGCACGC  TCCGCCAGTC  CCAAGGGTGC  GCAACCGGCT  GCACTCCCCT  CCCGCGACCC        180

AGGGCCCGGG  AGCAGCCCCC  ATGACCCACA  CGCACGTCTG  CAGCAGCCCC  GCTCACGCCC        240

CGGCGAGCCT  CAACCCAGGC  GTCCTGCCCC  TGCTCTGACC  CCGGGTGGCC  CCTACCCCTG        300

GCGACCCCTC  ACGCACACAG  CCTCTCCCCC  ACCCCACCC   GCGCACGCAC  ACATGCAGAT        360

AACAGCCCCG  ACCCCCGGCC  AGAGCCGCAG  AGTCCCTGGG  CCACCCCGGC  CGCTCGCTGC        420

GCTGCGCCGC  ACCGCGCTGT  CCTCCCGGAG  CCGGACCGGG  GCCACCGCGC  CCGCTCTGCT        480

CCGACACCGC  GCCCCTGGA   CAGCCGCCCT  CTCCTCTAGG  CCCGTGGGGC  TGGCCCTGCA        540

CCGCCGAGCT  TCCCGGGATG  AGGGCCCCCG  GTGTGGTCAC  CCGGCGCGCC  CCAGGTCGCT        600
```

GAGGGACCCC  GGCCAGGCGC  GGAG ATG  GGG  GTG  CAC   G GTGAGTACTC           647
                           Met Gly  Val  His
                           - 27      - 25

```
GCGGGCTGGG  CGCTCCCGCC  GCCCGGGTCC  CTGTTGAGC   GGGGATTTAG  CGCCCCGGCT        707

ATTGGCCAGG  AGGTGGCTGG  GTTCAAGGAC  CGGCGACTTG  TCAAGGACCC  CGGAAGGGGG        767

AGGGGGGTGG  GGCAGCCTCC  ACGTGCCAGC  GGGGACTTGG  GGGAGTCCTT  GGGGATGGCA        827

AAAACCTGAC  CTGTGAAGGG  GACACAGTTT  GGGGGTTGAG  GGGAAGAAGG  TTTGGGGGTT        887

CTGCTGTGCC  AGTGGAGAGG  AAGCTGATAA  GCTGATAACC  TGGGCGCTGG  AGCCACCACT        947

TATCTGCCAG  AGGGGAAGCC  TCTGTCACAC  CAGGATTGAA  GTTTGGCCGG  AGAAGTGGAT       1007

GCTGGTAGCT  GGGGGTGGGG  TGTGCACACG  GCAGCAGGAT  TGAATGAAGG  CCAGGGAGGC       1067

AGCACCTGAG  TGCTTGCATG  GTTGGGGACA  GGAAGGACGA  GCTGGGGCAG  AGACGTGGGG       1127

ATGAAGGAAG  CTGTCCTTCC  ACAGCACCC   TTCTCCCTCC  CCGCCTGACT  CTCAGCCTGG       1187
```

CTATCTGTTC  TAG  AA TGT  CCT  GCC  TGG  CTG  TGG  CTT  CTC  CTG  TCC  CTG    1235
              Glu Cys  Pro  Ala  Trp  Leu  Trp  Leu  Leu  Leu  Ser  Leu
              - 22       - 20                        - 15

| | | | | | | | | | | | | | | | | |
|---|---|---|---|---|---|---|---|---|---|---|---|---|---|---|---|---|
| CTG | TCG | CTC | CCT | CTG | GGC | CTC | CCA | GTC | CTG | GGC | GCC | CCA | CCA | CGC | CTC | 1283 |
| Leu | Ser | Leu | Pro | Leu | Gly | Leu | Pro | Val | Leu | Gly | Ala | Pro | Pro | Arg | Leu | |
| | | -10 | | | | -5 | | | | 1 | | | | | 5 | |
| ATC | TGT | GAC | AGC | CGA | GTC | CTG | GAG | AGG | TAC | CTC | TTG | GAG | GCC | AAG | GAG | 1331 |
| Ile | Cys | Asp | Ser | Arg | Val | Leu | Glu | Arg | Tyr | Leu | Leu | Glu | Ala | Lys | Glu | |
| | | | | 10 | | | | 15 | | | | | 20 | | | |
| GCC | GAG | AAT | ATC | ACG | GTGAGACCCC | | TTCCCCAGCA | | CATTCCACAG | | AACTCACGCT | | | | | 1386 |
| Ala | Glu | Asn | Ile | Thr | | | | | | | | | | | | |
| | | | | 25 | | | | | | | | | | | | |

CAGGGCTTCA GGGAACTCCT CCCAGATCCA GGAACCTGGC ACTTGGTTTG GGTGGAGTT 1446

GGGAAGCTAG ACACTGCCCC CCTACATAAG AATAAGTCTG GTGGCCCCAA ACCATACCTG 1506

GAAACTAGGC AAGGAGCAAA GCCAGCAGAT CCTACGGCCT GTGGGCCAGG GCCAGAGCCT 1566

| | | | | | | | | | | | | | | |
|---|---|---|---|---|---|---|---|---|---|---|---|---|---|---|
| TCAGGGACCC | TTGACTCCCC | GGGCTGTGTG | CATTTCAG | ACG | GGC | TGT | GCT | GAA | | | | | | 1619 |
| | | | | Thr | Gly | Cys | Ala | Glu | | | | | | |
| | | | | | | | | 30 | | | | | | |
| CAC | TGC | AGC | TTG | AAT | GAG | AAT | ATC | ACT | GTC | CCA | GAC | ACC | AAA | GTT | AAT | 1667 |
| His | Cys | Ser | Leu | Asn | Glu | Asn | Ile | Thr | Val | Pro | Asp | Thr | Lys | Val | Asn | |
| | | | 35 | | | | 40 | | | | | 45 | | | | |
| TTC | TAT | GCC | TGG | AAG | AGG | ATG | GAG | GTGAGTTCCT | | TTTTTTTTT | | TTTTCCTTTC | | | | 1721 |
| Phe | Tyr | Ala | Trp | Lys | Arg | Met | Glu | | | | | | | | | |
| | | | 50 | | | | 55 | | | | | | | | | |

TTTTGGAGAA TCTCATTTGC GAGCCTGATT TTGGATGAAA GGGAGAATGA TCGGGGGAAA 1781

GGTAAAATGG AGCAGCAGAG ATGAGGCTGC CTGGGCGCAG AGGCTCACGT CTATAATCCC 1841

AGGCTGAGAT GGCCGAGATG GGAGAATTGC TTGAGCCCTG GAGTTTCAGA CCAACCTAGG 1901

CAGCATAGTG AGATCCCCCA TCTCTACAAA CATTTAAAAA AATTAGTCAG GTGAAGTGGT 1961

GCATGGTGGT AGTCCCAGAT ATTTGGAAGG CTGAGGCGGG AGGATCGCTT GAGCCCAGGA 2021

ATTTGAGGCT GCAGTGAGCT GTGATCACAC CACTGCACTC CAGCCTCAGT GACAGAGTGA 2081

GGCCCTGTCT CAAAAAAGAA AAGAAAAAAG AAAAATAATG AGGGCTGTAT GGAATACATT 2141

CATTATTCAT TCACTCACTC ACTCACTCAT TCATTCATTC ATTCATTCAA CAAGTCTTAT 2201

TGCATACCTT CTGTTTGCTC AGCTTGGTGC TTGGGGCTGC TGAGGGCAG GAGGGAGAGG 2261

| | | | | | | | | |
|---|---|---|---|---|---|---|---|---|
| GTGACATGGG | TCAGCTGACT | CCCAGAGTCC | ACTCCCTGTA | G | GTC | GGG | CAG | CAG | 2314 |
| | | | | | Val | Gly | Gln | Gln | |

| | | | | | | | | | | | | | | | | |
|---|---|---|---|---|---|---|---|---|---|---|---|---|---|---|---|---|
| GCC | GTA | GAA | GTC | TGG | CAG | GGC | CTG | GCC | CTG | CTG | TCG | GAA | GCT | GTC | CTG | 2362 |
| Ala | Val | Glu | Val | Trp | Gln | Gly | Leu | Ala | Leu | Leu | Ser | Glu | Ala | Val | Leu | |
| 60 | | | | 65 | | | | | 70 | | | | | 75 | | |
| CGG | GGC | CAG | GCC | CTG | TTG | GTC | AAC | TCT | TCC | CAG | CCG | TGG | GAG | CCC | CTG | 2410 |
| Arg | Gly | Gln | Ala | Leu | Leu | Val | Asn | Ser | Ser | Gln | Pro | Trp | Glu | Pro | Leu | |
| | | | 80 | | | | | 85 | | | | | 90 | | | |
| CAG | CTG | CAT | GTG | GAT | AAA | GCC | GTC | AGT | GGC | CTT | CGC | AGC | CTC | ACC | ACT | 2458 |
| Gln | Leu | His | Val | Asp | Lys | Ala | Val | Ser | Gly | Leu | Arg | Ser | Leu | Thr | Thr | |
| | | | 95 | | | | 100 | | | | | 105 | | | | |
| CTG | CTT | CGG | GCT | CTG | GGA | GCC | CAG | GTGAGTAGGA | | GCGGACACTT | | CTGCTTGCCC | | | | 2512 |
| Leu | Leu | Arg | Ala | Leu | Gly | Ala | Gln | | | | | | | | | |
| | | 110 | | | | 115 | | | | | | | | | | |

TTTCTGTAAG AAGGGGAGAA GGGTCTTGCT AAGGAGTACA GGAACTGTCC GTATTCCTTC 2572

| | | | | | | | | |
|---|---|---|---|---|---|---|---|---|---|
| CCTTTCTGTG | GCACTGCAGC | GACCTCCTGT | TTTCTCCTTG | GCAG | AAG | GAA | GCC | ATC | 2628 |
| | | | | | Lys | Glu | Ala | Ile | |

| | | | | | | | | | | | | | | | | |
|---|---|---|---|---|---|---|---|---|---|---|---|---|---|---|---|---|
| TCC | CCT | CCA | GAT | GCG | GCC | TCA | GCT | GCT | CCA | CTC | CGA | ACA | ATC | ACT | GCT | 2676 |
| Ser | Pro | Pro | Asp | Ala | Ala | Ser | Ala | Ala | Pro | Leu | Arg | Thr | Ile | Thr | Ala | |
| 120 | | | | | 125 | | | | | 130 | | | | | 135 | |
| GAC | ACT | TTC | CGC | AAA | CTC | TTC | CGA | GTC | TAC | TCC | AAT | TTC | CTC | CGG | GGA | 2724 |
| Asp | Thr | Phe | Arg | Lys | Leu | Phe | Arg | Val | Tyr | Ser | Asn | Phe | Leu | Arg | Gly | |
| | | | | 140 | | | | | 145 | | | | | 150 | | |

```
AAG CTG AAG CTG TAC ACA GGG GAG GCC TGC AGG ACA GGG GAC AGA
Lys Leu Lys Leu Tyr Thr Gly Glu Ala Cys Arg Thr Gly Asp Arg
            155                 160                 165

TGACCAGGTG                                                                      2779

TGTCCACCTG  GGCATATCCA  CCACCTCCCT  CACCAACATT  GCTTGTGCCA  CACCCTCCCC          2839

CGCCACTCCT  GAACCCCGTC  GAGGGGCTCT  CAGCTCAGCG  CCAGCCTGTC  CCATGGACAC          2899

TCCAGTGCCA  GCAATGACAT  CTCAGGGGCC  AGAGGAACTG  TCCAGAGAGC  AACTCTGAGA          2959

TCTAAGGATG  TCACAGGGCC  AACTTGAGGG  CCCAGAGCAG  GAAGCATTCA  GAGAGCAGCT          3019

TTAAACTCAG  GGACAGAGCC  ATGCTGGGAA  GACGCCTGAG  CTCACTCGGC  ACCCTGCAAA          3079

ATTTGATGCC  AGGACACGCT  TTGGAGGCGA  TTTACCTGTT  TTCGCACCTA  CCATCAGGGA          3139

CAGGATGACC  TGGAGAACTT  AGGTGGCAAG  CTGTGACTTC  TCCAGGTCTC  ACGGGCATGG          3199

GCACTCCCTT  GGTGGCAAGA  GCCCCCTTGA  CACCGGGGTG  GTGGGAACCA  TGAAGACAGG          3259

ATGGGGGCTG  GCCTCTGGCT  CTCATGGGGT  CCAAGTTTTG  TGTATTCTTC  AACCTCATTG          3319

ACAAGAACTG  AAACCACCAA  TATGACTCTT  GGCTTTTCTG  TTTTCTGGGA  ACCTCCAAAT          3379

CCCCTGGCTC  TGTCCCACTC  CTGGCAGCAG  TGCAGCAGGT  CCAGGTCCGG  GAAATGAGGG          3439

GTGGAGGGGG  CTGGGCCCTA  CGTGCTGTCT  CACACAGCCT  GTCTGACCTC  TCGACCTACC          3499

GGCCTAGGCC  ACAAGCTCTG  CCTACGCTGG  TCAATAAGGT  GTCTCCATTC  AAGGCCTCAC          3559

CGCAGTAAGG  CAGCTGCCAA  CCCTGCCCAG  GGCAAGGCTG  CAG                            3602
```

( 2 ) INFORMATION FOR SEQ ID NO:34:

( i ) SEQUENCE CHARACTERISTICS:
        ( A ) LENGTH: 193 amino acids
        ( B ) TYPE: amino acid
        ( D ) TOPOLOGY: linear ( i i ) MOLECULE TYPE: protein ( x i ) SEQUENCE DESCRIPTION: SEQ ID NO:34:

```
Met Gly Val His Glu Cys Pro Ala Trp Leu Trp Leu Leu Leu Ser Leu
-27         -25             -20                     -15

Leu Ser Leu Pro Leu Gly Leu Pro Val Leu Gly Ala Pro Pro Arg Leu
        -10              -5                   1                  5

Ile Cys Asp Ser Arg Val Leu Glu Arg Tyr Leu Leu Glu Ala Lys Glu
                 10              15                    20

Ala Glu Asn Ile Thr Thr Gly Cys Ala Glu His Cys Ser Leu Asn Glu
             25              30              35

Asn Ile Thr Val Pro Asp Thr Lys Val Asn Phe Tyr Ala Trp Lys Arg
        40              45              50

Met Glu Val Gly Gln Gln Ala Val Glu Val Trp Gln Gly Leu Ala Leu
    55              60              65

Leu Ser Glu Ala Val Leu Arg Gly Gln Ala Leu Leu Val Asn Ser Ser
70              75              80                  85

Gln Pro Trp Glu Pro Leu Gln Leu His Val Asp Lys Ala Val Ser Gly
                90              95              100

Leu Arg Ser Leu Thr Thr Leu Leu Arg Ala Leu Gly Ala Gln Lys Glu
            105             110             115

Ala Ile Ser Pro Pro Asp Ala Ala Ser Ala Ala Pro Leu Arg Thr Ile
            120             125             130

Thr Ala Asp Thr Phe Arg Lys Leu Phe Arg Val Tyr Ser Asn Phe Leu
            135             140             145
```

| Arg | Gly | Lys | Leu | Lys | Leu | Tyr | Thr | Gly | Glu | Ala | Cys | Arg | Thr | Gly | Asp |
| 150 | | | | | 155 | | | | | 160 | | | | | 165 |

Arg (2) INFORMATION FOR SEQ ID NO:35:

(i) SEQUENCE CHARACTERISTICS:
        (A) LENGTH: 788 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (vii) IMMEDIATE SOURCE:
        (B) CLONE: EPOlong (xi) SEQUENCE DESCRIPTION: SEQ ID NO:35:

```
AGCTTGCCCG GGATGAGGGC CACCGGTGTG GTCACCCGGC GCGCCCCAGG TCGCTGAGGG      60
ACCCCGGCCA GGCGCGGAGA TGGGGGTGCA CGAATGTCCT GCCTGGCTGT GGCTTCTCCT     120
GTCCCTGCTG TCGCTCCCTC TGGGCCTCCC AGTCCTGGGC GCCCCACCAC GCCTCATCTG     180
TGACAGCCGA GTCCTGGAGA GGTACCTCTT GGAGGCCAAG GAGGCCGAGA ATATCACGAC     240
GGGCTGTGCT GAACATTGCA GCTTGAATGA GAATATCACT GTCCAGACA CCAAAGTTAA      300
TTTCTATGCC TGGAAGAGGA TGGAGGTCGG GCAGCAGGCC GTAGAAGTCT GGCAGGGCCT     360
GGCCCTGCTG TCGGAAGCTG TCCTGCGGGG CCAGGCCCTG TTGGTCAACT CTTCCCAGCC     420
GTGGGAGCCC CTGCAGCTGC ATGTGGATAA AGCCGTCAGT GGCCTTCGCA GCCTCACCAC     480
TCTGCTTCGG GCTCTGGGAG CCCAGAAGGA AGCCATCTCC CCTCCAGATG CGGCCTCAGC     540
TGCTCCACTC CGAACAATCA CTGCTGACAC TTTCCGCAAA CTCTTCCGAG TCTACTCCAA     600
TTTCCTCCGG GGAAAGCTGA AGCTGTACAC AGGGGAGGCC TGCAGGACAG GGACAGATG      660
ACCAGGTGTG TCCACCTGGG CATATCCACC ACCTCCCTCA CCAATATTGC TTGTGCCACA     720
CCCTCCCCCG CCACTCCTGA ACCCGTCGA GGGGCTCTCA GCTCAGCGCC AGCCTGTCCC      780
ATGGACCA                                                             788
```

(2) INFORMATION FOR SEQ ID NO:36:

(i) SEQUENCE CHARACTERISTICS:
        (A) LENGTH: 605 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (vii) IMMEDIATE SOURCE:
        (B) CLONE: Rh 32

(xi) SEQUENCE DESCRIPTION: SEQ ID NO:36:

```
AAAAAGATGA GGTAATTGTG TTTTTATAAT TAAATATTTT ATAATTAAAA TATTTATAAT      60
TAAAATATTT ATAATTAAAT ATTTTATAAT TAAAATATTT ATAATTAAAT ATTTTATAAT     120
TAAAATATTT ATAATTAAAT ATTTTATAAT TAAAATATTT ATAATTAAAT ATTTTATAAT     180
TAAAATATTT ATAATTAAAT ATTTTATAAT TAAAATATTT ATAATTAAAT ATTTTATAAT     240
TAAAATATTT ATAATTAAAT ATTTTATAAT TAAAATGTTT ATAATTACAT ATTTTATAAT     300
```

| TAAAATGTTT | ATAATTACAT | ATTTTATAAT | TAAAATGTTT | ATAATTACAT | ATTTTATAAT | 360 |
| TAAAATGTTT | ATAATTACAT | ATTTTATAAT | TACATATTTT | ATAAAGTATT | TATAATTACA | 420 |
| TATTTTATAA | TTAAAGTATT | TATAATTACA | TATTTTATAA | TTAAAGTATT | TATAATTACA | 480 |
| TATTTTATAA | TTCAATATTT | TATAAATAGT | TAAAAGACG | AGGAAAAAAT | TAAAAGACG | 540 |
| AGGTTATTGA | TCTCAGGAAT | TGTATTTGCC | AAGTGAGAAG | GAAAAAATAT | TCACAAAGGC | 600 |
| TTGTA | | | | | | 605 |

( 2 ) INFORMATION FOR SEQ ID NO:37:

( i ) SEQUENCE CHARACTERISTICS:
        ( A ) LENGTH: 2529 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: Rh 10

( x i ) SEQUENCE DESCRIPTION: SEQ ID NO:37:

| TCTAGACCCC | AGTTTCTCTA | TAAGATGAGA | ATATTAGTCA | CGATTTGGTT | TCTAAGATCC | 60 |
| TGTCTATGTT | TGAGACTACA | GATACCTGTT | GCTACATTTC | CCTTCATAGC | TCTGAACAAG | 120 |
| GAGAATTCAG | CCCAATTCTC | ATGGCCTTCT | AAACAATCCA | GAGTTTCAGT | GCCATAAGGT | 180 |
| ACTACAATTT | AGTGTCAAAT | TAAGTCAAAG | GCTTCATTAG | CCTGAAAGCT | CTGTCCCTGG | 240 |
| CCTGGGCATG | GCAAACTGTA | TCCCCCACTG | ACCATCCCCC | TGTCTCCCTT | CTCCCCAGAG | 300 |
| ACTCCAGTAG | CCTGGCGTCA | TCACAGGGGC | CAGACATATC | CAACATGTTC | CCAGCTTCCT | 360 |
| GCCACTTGAC | TTTCAGTGTG | CCTCCCTCTT | CAGTTACCCA | AATCCTGCCC | ACCATTCCAG | 420 |
| AGCCAGTTCA | ATCTCACCCA | TCCAGGACCC | CCGAGACCCC | CATCGTACCA | CTATAGTCTA | 480 |
| ACTGTGGTGT | AGACCCCACA | CTGGGCACAT | TGCGTACGCT | CATTATTGGC | TGTGACGTCT | 540 |
| GATTATGCCC | TTCTCCTGGT | CTGGAAGCTC | TCGGAGGTGC | TCCATAATAC | ATGAAGAGAA | 600 |
| GTAGTGCTGG | TGTGGGAATA | GTGAGGTGTG | TTTATCCATC | CAGCTATCCG | GCACCAGCAC | 660 |
| TGGTCTCAGC | TTTCTGAGGT | AACACGTTCT | GAGCCTTAGT | CTTGAGAGAA | CATAAAGAAA | 720 |
| ACTTTTTTTA | AAAGTAGTAA | AAAGTGGCTG | ACAAAAGCTG | ACCAAAAGCC | TTCAAAAGAA | 780 |
| ATGCTAAGTT | ATATCTAAGA | AAGTTTACCC | AAGGTCAGGC | AAATATGAAA | CCTAAAGCTA | 840 |
| GACGTGGGGA | AGAACTTCCG | GAGAGTTGCA | ATTCCCTGTG | CCCCAGCATC | CCCAGGAGGG | 900 |
| CATGCCCACA | TCTGATTTAG | AAATCTGTGT | AAAATGAGTG | AAGGTTTCTA | TTTCTTGGGC | 960 |
| AGTGTGGGCA | CAGGTCTTTG | GAGAGGTCGA | TGGCCTCCCA | TAAAATCCTT | CCTGCTTGAT | 1020 |
| GGTTCTGGAT | CCTCAGCCAC | AGCTCCTAAT | AGCCATGAGG | TTTGAGCCCA | AAATAATTTA | 1080 |
| TGTGTTTGTT | TTTTCAGCCC | CAAAATTTCC | ATAGAATCAA | AGTAGTCAGA | GCTGAATGGG | 1140 |
| GCTAAGAGAC | CGTCCATTCC | TGTCTTCTCA | TCACAGATGA | GGGACTGCCA | CCCAGAGCCG | 1200 |
| TAGAAACTGT | CCCATGGCCC | CAGTTCCCAG | ACCCTTCCTC | TCTCCTACAG | CTCCAAGTTC | 1260 |
| ACTGTGCATT | CTAAATGAAG | ATGTAAACAT | AGGCAGCAAC | ACTCAAGAGT | AAAAATGAAG | 1320 |
| TGTGCATATG | AAAGAAACCT | ATTCACATGG | ACCATATTAC | ATTATAATCA | CAGTGTTTAC | 1380 |
| TGCTTGACTA | CCATCTGCCT | GGGCTAGCAA | GGGTGTCAGT | GAGGAAGAGA | GGACAAGGGG | 1440 |

-continued

| | | | | | | |
|---|---|---|---|---|---|---|
| TACCAATCTG | TGAACTACAC | ATGGTTCTTG | CTCTCCAGC | TTCTCTCTCC | CATTGGCAAG | 1500 |
| GCAACAGGTA | AACACATGAA | AAATCAAATA | ATGCTATAAG | AGAAAAATGT | ATTCAGGACA | 1560 |
| ACAACAGGTT | TGTATGAAGG | CCTTTCATCA | TCGTTGTCCT | ACCTAGAAAC | TGAATGACAG | 1620 |
| GGAATCAGAG | TCACAAGCTA | TGAAGTCTAA | CTGGGCTGGT | CCCAGAGAAA | GATTCAGTGC | 1680 |
| AGTAGGTGGG | GCTGCAGCCA | GCCCTGGGTG | GGTGGAAGGA | TGACATCCAC | ATAGGCAAGA | 1740 |
| GGGTGATAAT | TCACTTGCGC | AGCTCCTCAC | TGCACATTGA | ACCCTGCTGA | CTTCTGGCTT | 1800 |
| CTCTCCCGGG | AGGAACTGCG | ACTCAACATT | CTGACCTTAT | CTCTTGGGTA | GCAGAATGAT | 1860 |
| GGAGAAGGAA | AGTTTCTTTT | TGCTTCTCGC | AGGGGTTAAT | CATCCATCTG | GAATGCCTAC | 1920 |
| ATTTGGTTGA | CAATGGCTCA | CCCTATCATC | TTCCTCCTGA | ACCATTCACC | TAAATGTGCC | 1980 |
| ATTTCTTTCC | TGATAGTTCT | CATTTGTGTG | TGTGTGTGTG | TGTGTGTGTG | TGCACGTGCT | 2040 |
| CACACATGCA | TGCTGTCACT | GGGTAAACAG | GCCACCCTGG | GCACAGTTCC | ATCTACAATG | 2100 |
| TTTGAAGTTT | ACTTTCCAGC | TTCTGGGCAT | CATTTGCAAT | TATAATGCTG | TCACAGGCAG | 2160 |
| AAACGAGATA | GGCTAATTAA | TCGTTGTCAA | TACTGATCCC | TATTTGCCAG | ATGAGATTTT | 2220 |
| GGAGCAGCAT | GGCTGGGAAT | AATTGGTATA | GACTGTATTT | CCTTGCTTTA | TGTCACTGGA | 2280 |
| AATATTTATT | TAAGCATCAC | GGTCGCTATG | CATAAATATC | CTGGAAAATG | GGGTATAGCT | 2340 |
| GAATGGTGCA | GATTCATTCA | TTCATATTCA | GCAAATTATG | TTCTAAGCAC | CTACTTCAGT | 2400 |
| ACGTGAACAG | CACTAAACTC | AGAATATTGG | TCTGCTGGGG | TCCTTTATTA | GCTTCCATGA | 2460 |
| TTCCCTGAAC | TTGGCCAAGA | CCCTTCTGGT | CGGCTGCAGA | TAGGCACAAT | GGATAGTTTT | 2520 |
| GCTTCTAGA | | | | | | 2529 |

I claim:

1. A recombinant DNA molecule adapted for expression of erythropoietin, comprising a nucleic acid molecule encoding mammalian erythropoietin, an expression control sequence operatively linked thereto and at least one human apolipoprotein B SAR element.

2. A recombinant DNA molecule as claimed in claim 1 wherein the nucleic acid molecule encodes human erythropoietin.

3. A recombinant DNA molecule as claimed in claim 2 wherein the nucleic acid molecule encodes erythropoietin having the amino acid sequence shown in SEQ ID NO 34.

4. A recombinant DNA molecule as claimed in claim 3 wherein the nucleic acid molecule has the sequence as shown in SEQ ID NO. 35.

5. A recombinant DNA molecule as claimed in claim 1 wherein the SAR element comprises the sequence as shown in SEQ ID NO. 36 or 37.

6. A recombinant DNA molecule as claimed in claim 1 wherein the nucleic acid molecule encoding mammalian erythropoietin and the expression control sequence operatively linked thereto are flanked by SAR elements.

7. An expression vector comprising a recombinant DNA molecule as claimed in claim 1.

8. An expression vector comprising a nucleic acid molecule encoding erythropoietin and having the sequence shown in SEQ ID NO.35 under the control of a promoter, flanked by 5' and 3' human apolipoprotein B SAR elements.

9. An expression vector as claimed in claim 8 wherein the promoter is a human cytomegalovirus IE enhancer and promoter, or an elongation factor-1 alpha promoter.

10. A mammalian cell transformed with an expression vector as claimed in claim 7.

11. A mammalian cell as claimed in claim 10 lacking a selectable gene capable of being amplified, said cell being capable of expressing recombinant erythropoietin in vitro at levels of at least about 2,000 u/$10^6$ cells in 24 hours.

12. A method of expressing recombinant mammalian erythropoietin comprising the steps of culturing a mammalian cell as claimed in claim 11 in a suitable medium until sufficient amounts of erythropoietin are produced by the cell and separating the erythropoietin produced.

13. A method of preparing recombinant erythropoietin comprising transfecting a mammalian cell with an expression vector comprising a recombinant DNA molecule as claimed in claim 1, and culturing the transfected cell in a suitable medium until sufficient amounts of erythropoietin are produced by the cell and separating the erythropoietin produced.

14. A method as claimed in claim 12 wherein the mammalian cell is further transfected with a selectable marker gene and wherein transfected cells are selected by means of the selectable marker gene.

15. A method as claimed in claim 14 wherein the selectable marker gene is neo.

16. A method as claimed in claim 12 comprising the additional step of identifying and selecting cells producing high levels of erythropoietin; subcloning the selected cells; establishing long term cell lines from the selected cells and; culturing the selected cells in a suitable medium until sufficient amounts of erythropoietin are produced by the cell and separating the erythropoietin produced.

17. A method as claimed in claim 12 wherein erythropoietin is produced at levels of at least 1,500 u/$10^6$ cells in 24 hours in the absence of gene amplification.

* * * * *